United States Patent
Paul et al.

(10) Patent No.: US 7,625,712 B2
(45) Date of Patent: Dec. 1, 2009

(54) METHOD FOR A FULLY AUTOMATED MONOCLONAL ANTIBODY-BASED EXTENDED DIFFERENTIAL

(75) Inventors: Ronald D. Paul, Fort Lauderdale, FL (US); James L. Wyatt, San Diego, CA (US); Barbara Carrillo, Miami, FL (US); Oilda Rubio, Miami, FL (US); Diana B. Careaga, Miami, FL (US); Lidice L. Lopez, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 351 days.

(21) Appl. No.: 11/130,492

(22) Filed: May 17, 2005

(65) Prior Publication Data

US 2005/0260766 A1  Nov. 24, 2005

Related U.S. Application Data

(60) Provisional application No. 60/573,167, filed on May 21, 2004.

(51) Int. Cl.
  *G01N 33/567* (2006.01)
(52) U.S. Cl. ............... 435/7.21; 435/7.23; 435/7.24; 435/285.2; 435/287.1; 435/287.2; 435/288.7; 436/10; 436/17; 436/56; 436/164; 436/171; 436/175; 436/546; 422/82.01; 422/82.05; 422/82.07
(58) Field of Classification Search ............ 435/2, 435/7.24, 7.25, 40.5, 239, 285.2, 87.1, 287.2, 435/288.7, 962, 7.21, 7.23, 287.1; 436/10, 436/17, 56, 63, 164, 165, 171, 174, 175, 436/176, 177, 526, 532, 533, 546, 536; 422/82.01, 422/82.05, 82.06, 82.07, 90, 91
See application file for complete search history.

(56) References Cited

U.S. PATENT DOCUMENTS 3,962,125 A  6/1976 Armstrong (Continued)

FOREIGN PATENT DOCUMENTS

EP  0317156  5/1989
EP  1363126  11/2003

OTHER PUBLICATIONS

Fujimoto et al., Flow Cytometric Method for Enumeration and Classification of Reactive Immature Granulocyte Populations, Cytometry (Communications in Clinical Cytometry) 42: 371-378 (2000).*

(Continued)

*Primary Examiner*—Gailene R Gabel
(74) *Attorney, Agent, or Firm*—Howson & Howson LLP; Mitchell E. Alter, Esq.

(57) ABSTRACT

A method useful for the enumeration of cell populations in a biological sample includes the steps of reacting in a single reaction mixture a sample, a first antibody labeled with a fluorochrome having a first emission spectrum and an additional antibody. The first antibody binds to an antigenic determinant differentially expressed on leukocytes and non-leukocytes. The additional antibody binds to an antigenic determinant differentially expressed on mature and immature granulocytes or myeloid cells, and is labeled either with the first fluorochrome or an additional fluorochrome having an emission spectrum distinguishable from the first emission spectrum. The reaction mixture can be mixed with a nucleic acid dye having an emission spectrum that overlaps with one of the first or additional emission spectra. The reaction mixture may be treated with a lytic system that differentially lyses non-nucleated red blood cells and conserves leukocytes. Populations of hematological cells are detected and enumerated using at least two parameters (fluorescence, optical, and electrical) for each population.

14 Claims, 10 Drawing Sheets

U.S. PATENT DOCUMENTS

| | | | |
|---|---|---|---|
| 5,030,554 | A | 7/1991 | Quintana et al. |
| 5,047,321 | A | 9/1991 | Loken et al. |
| 5,064,616 | A | 11/1991 | Brosnan et al. |
| 5,125,737 | A | 6/1992 | Rodriguez et al. |
| 5,137,809 | A | 8/1992 | Loken et al. |
| 5,164,311 | A | 11/1992 | Gupta |
| 5,234,816 | A | 8/1993 | Terstappen |
| 5,438,003 | A | 8/1995 | Colella et al. |
| 5,563,070 | A | 10/1996 | Yamamoto et al. |
| 5,565,499 | A | 10/1996 | Klemarczyk et al. |
| 5,631,165 | A | 5/1997 | Chupp et al. |
| 5,633,167 | A | 5/1997 | Fan et al. |
| 5,648,225 | A * | 7/1997 | Kim et al. .................. 435/7.24 |
| 5,763,280 | A | 6/1998 | Li et al. |
| 5,776,709 | A | 7/1998 | Jackson et al. |
| 5,812,419 | A | 9/1998 | Chupp et al. |
| 5,882,933 | A | 3/1999 | Li et al. |
| 6,197,593 | B1 * | 3/2001 | Deka et al. .................... 436/63 |
| 6,228,532 | B1 | 5/2001 | Tsuji et al. |
| 6,228,652 | B1 * | 5/2001 | Rodriguez et al. ............ 436/63 |
| 6,461,825 | B1 | 10/2002 | Carriere |
| 6,573,102 | B2 | 6/2003 | Li et al. |
| 6,692,968 | B2 | 2/2004 | Burshteyn et al. |
| 6,900,023 | B1 * | 5/2005 | Houwen et al. ............ 435/7.24 |
| 6,911,313 | B2 * | 6/2005 | Houwen et al. .............. 435/7.2 |
| 2006/0269970 | A1 | 11/2006 | Paul et al. |

OTHER PUBLICATIONS

Thomas et al., Combined Optical and Electronic Analysis of cells with AMAC transducers, The Journal of Histochemistry Cytochemistry, 25 (7): 827-835 (1977).*

Bowen et al., Abnormal patterns of expression of CD16 (FcRylll) and CD11b (CRlll) antigens by developing neutrophils in the bond marrow of patients with myelodysplastic syndrome, Laboratory Hematology 3: 292-298 (1997).*

Civin, C.I., et al., "Cell Surface Antigens on Human Marrow Cells: Dissection of Hematopoietic Development Using Monoclonal Antibodies and . . . ", Intl. J Cell Cloning, vol. 5, pp. 267-288 (1987).

Fujimoto, H., et al., "Flow cytometric method for enumeration and classification of reactive immature granulocyte populations", Cytometry 42, pp. 371-378 (2000).

Goossens, W., et al., "Preliminary data on the feasibility of bone marrow screening on the Sysmex XE-2100 automated hematology analyzer", Sysmez J Intl, 11(2), pp. 70-73 (2001).

Stockert, Juan C., "Cytochemistry of mast cells: new fluorescent methods selective for sulfated glycosaminoglycans", Acta Histochem, 102, pp. 259-272 (2000).

Thomas, R.A., et al., "Combined Optical and Electronic Analysis of Cells with the AMAC Transducers", J Histochem and Cytochem, vol. 25, No. 7, pp. 827-835 (1977).

Weiland, T., et al., "Evaluation of the Automated Immature Granulocyte Count (IG) on Sysmex XE-2100 Automated Haematology Analyser vs . . . " Sysmex J Intl., 12(2), pp. 63-70 (2002).

Burgess, "Continuing Absolute Numbers of Specific Leukocyte Subpopulations in Avian Whole Blood Using a Single-Step Flow Cytomeric Technique: Comparison of Two Inbred Lines of Chickens", J of Immunol, 227 (1-2):169-176 (Jul. 30, 1999).

Macey, "The Q-Prep System: Effects of the Apparent Expression of Leucocyte Cell Surface Antigens", Cytometry, 30(2):67-71 (Apr. 15, 1997).

European Search Report in European Patent Application No. 05754002.3 (Apr. 25, 2008).

* cited by examiner

METHOD FOR A FULLY AUTOMATED MONOCLONAL ANTIBODY-BASED EXTENDED DIFFERENTIAL

CROSS REFERENCE TO RELATED APPLICATIONS

This application claims the benefit of the priority of U.S. Provisional Patent Application No. 60/573,167, filed May 21, 2004.

BACKGROUND OF THE INVENTION

The present invention relates to improvements in methods for differentiating and enumerating the various constituent subpopulations or types of hematological cells in biological samples, and more particularly, to high throughput, automated systems for this purpose.

In general, whole blood and peripheral blood samples from human subjects suffering from a variety of diseases can contain both blood cells or non-blood cells (e.g., tumor cells, bacteria, etc.), suspended in a liquid medium or plasma. The blood cells include red blood cells (erythrocytes or RBCs), white blood cells (leukocytes or WBCs), and platelets. Depending on the level of maturity of the cells, red cells are further classified into three subsets, namely, nucleated RBCs (NRBC's), reticulated RBCs (reticulocytes), and mature RBCs. Mature white cells fall into one of five different categories, namely, monocytes, lymphocytes, eosinophils, neutrophils and basophils. Each of the white cell subsets can be further classified into subclasses based on their respective level of maturity, activation, lineage, function, phenotype, or abnormality. Typically, only mature cells are normally present in peripheral blood in detectable amounts. The number of red cells in a normal human outnumber the total number of white cells by about 1000:1. Platelets, which play a role in coagulation, are of three general types, megakaryocytes, immature reticulated platelets and mature platelets.

The differentiation and enumeration of these various types of blood cells and platelets in a patient's peripheral blood, as well as the determination of certain parameters or characteristics thereof, permits diagnosis of a variety of hematological disorders or diseases. The absolute numbers, concentrations and relative percentages of the different types of blood cells are highly indicative of the presence or absence and/or stage of certain disease states.

Current commercially available, high throughput hematology flow analyzers provide a number of measured and mathematically derived cellular indices on red blood cells, platelets and white blood cells in peripheral blood specimens. The detection and enumeration of primarily mature cell types, as well as a determination of additional cell parameters, can be accomplished by using any one of several commercially available hematology instruments, including e.g., Beckman Coulter's LH 750™, GEN S™, STKS™, and MAXM™ hematology instruments; Abbott Laboratories' Cell Dyne 3000/4000 hematology instruments; Sysmex System™ series of hematology instruments; ABX diagnostics instruments; and Bayer Technicon instruments. In automatically acquiring data on each cell type, most of the above-mentioned hematology instruments use at least two discrete cell-analyzing transducers. One (or more) of these transducers operate to acquire data useful in differentiating and enumerating the five different types of WBCs. Another transducer is dedicated to counting and sizing of RBCs, WBCs and platelets in a precise volume of sample. The respective outputs of the multiple transducers are processed by a central processing unit to provide an integrated cell analysis report. The respective outputs of the several transducers are correlated to provide the five-part differential information.

An "extended differential" measurement includes the normal "5-part differential" as well as the detection and enumeration of atypical cells (e.g., cells which are considered abnormal in relation to cells in healthy human blood) and immature cells. Due to the current limitations of commercially available hematology instruments, a skilled medical technologist must perform a microscopic examination (Manual Differential) in order to obtain an extended differential analysis. First a blood-smear of a sample of interest is produced manually on a glass microscope slide. Then the smear is stained with a dye to enable all cells including the atypical or immature cells of interest to be visually differentiated from each other. The resulting stained blood-smear is examined under a microscope.

Alternatively, some blood cell types of an extended differential measurement can be detected using a conventional flow cytometer. In such an instrument, a blood sample that has been previously prepared, e.g., by either (1) mixing the sample with fluorochrome-labeled monoclonal antibodies or the like which serve to selectively "tag" certain cells of interest, or (2) mixing the sample with a fluorescent stain adapted to selectively mark cells of interest, is passed through an optical flow cell. As each cell in the sample passes through the flow cell, it is irradiated with a beam of photons adapted to excite the fluorescent material associated with the cells of interest. Fluorescent light, emitted by each of the labeled cells, and light scattered by each cell are detected and used to differentiate the cells of interest from other cells in the sample.

In summary, conventional hematology instruments, while being capable of differentiating and enumerating the vast majority of cell types and subsets normally present in a peripheral blood sample, cannot readily differentiate multiple subsets of cells in a single sample, particularly those cells that are atypical or immature.

The ability to provide relevant information beyond the total white blood cell count is directly related to the inclusion of multiple analytical parameters within hematology systems. As described above, most current hematology systems identify normal blood cell populations by examining a combination of light scatter measurements or light scatter and electrical measurements collected in sequential analyses of the same reaction mixture (i.e., an aliquot of the same sample) or from analyses of different reaction mixtures of the same sample. Various configurations or combinations of electrical current impedance, conductivity, light scatter, absorbance, axial light loss and fluorescence have been used to determine the five-part differential, as well as to provide flagging information for the presence of atypical cell types by using different aliquots of the same sample.

Commercial, stand-alone, flow cytometers are manufactured by Beckman Coulter, Sysmex Corporation, Cytomation, Bio-Rad, and Becton Dickinson. Flow cytometers and hematology instruments have previously been integrated into a single automated laboratory system in which blood samples are automatically advanced along a track past these different instruments. As sample-containing vials pass each instrument, a blood sample is aspirated from each vial and analyzed by the instrument. Instrument systems combining discrete hematology and flow cytometry instruments are commercially available from Beckman Coulter and Sysmex Corporation, reference being made to Sysmex's HST Series. The requirement to correlate the respective outputs of multiple transducers in order to report certain characteristics of a cell type or subset can, under certain circumstances, be problematic, in that it introduces uncertainty in the analytical results (U.S. Pat. Nos. 5,631,165 and 5,565,499). The desirability of using a single electro-optical transducer to simultaneously measure the volume (V), conductivity (C), light scatter (S) and fluorescence (F) of a single cell has been suggested as offering the advantage of making all measurements simultaneously on the same cell, rather than making some measurements on one cell with one transducer, making other measurements on another cell of the same type using another transducer, and then attempting to correlate the results from the two transducers to draw certain conclusions about the cell sample (see, e.g., Thomas et al., J. Histochem. Cytochem., 25(7): 827-835 (1977)).

Fluorescence based flow cytometry has been used to determine leukocyte lineage and state of maturation. Traditional flow cytometric analysis of multiple qualitatively distinct antigenic determinants is usually performed by employing a distinct fluorochrome for each antibody utilized in the same analysis. Usually a series of analyses are performed in order to derive clinically relevant information. This requires a separate fluorescence detector, optics and electronics for each fluorochrome used and often the incorporation of more than one laser. For example, C. I. Civen et al, 1987 *Internat'l. J Cell Cloning,* 5:267-288 refers to the use of multiparameter flow cytometry to map expression of three cell surface antigens on erythroid cells in marrow aspirate preparations. U.S. Pat. No. 5,234,816 refers to a method for classifying and monitoring leukemias by mixing patient blood or bone marrow cells with a plurality of monoclonal antibodies to B, T, myeloid or undifferentiated cells, each antibody labeled with a fluorochrome having an emission spectra distinguishable from the other. Fluorescence intensities and light scatter parameters are measured by flow cytometry in a two-dimensional scattergram of log fluorescence. U.S. Pat. No. 5,137,809 refers to a method for identifying lineage and developmental stages of hematopoietic cells by treating the cells with labeled monoclonal antibodies which bind to antigenic sites on leukocytes, each antibody labeled with a fluorochrome having an emission spectrum distinguishable from the other and analyzing the cells by size, granularity and relative fluorescence intensity.

Of the technologies discussed, fluorescence based measurements have the potential to provide greater advances in hematocellular analysis. Unlike the other aforementioned technologies that take advantage of the differences in the intrinsic physical properties of cells, fluorescence detection can examine the extrinsic properties of cells through the use of probes such as fluorescent dyes, histochemical stains, and fluorescent conjugated hybridization probes or monoclonal antibodies. Fluorescence measurements have proven beneficial by providing a high degree of sensitivity and specificity through the selection of appropriate reagents. Fluorescence based flow cytometry systems have been utilized for a number of years in research environments and more recently in clinical laboratories for performing immunodeficiency analyses, DNA cell cycle analyses, and leukemia/lymphoma immunophenotyping. More recently, fluorescence measurements have been introduced on routine hematology flow systems initially for the purpose of enumerating reticulated RBCs (Sysmex, ABX and Abbott) followed by NRBC enumeration (Abbott and Sysmex). A fluorescence based immuno-platelet count has also recently been announced. Of the three fluorescence measurements that have been discussed, two (reticulocyte enumeration and immuno-platelet count) are either secondary or reflex mode measurements. The only measurement that occurs as part of the leukocyte differential cycle is NRBC enumeration on the Cell-Dyne 4000 apparatus. This analysis is performed utilizing a nucleic acid intercalating dye (propidium iodide) and light scatter to differentiate between intact WBCs, damaged WBCs and NRBCs.

Despite the application of these technologies, the currently available hematology systems still suffer from common shortcomings. These include difficulty in the performance of an accurate 5-part white blood cell differential in the presence of various atypical leukocyte populations or other abnormal conditions (cellular/non cellular) that interfere with performance of the 5-part differential. In addition, the correlations that permit the detection of, or flagging for, the presence of atypical cell types suffer from high false positive or high false negative rates. These shortcomings are unacceptable because they either result in an unnecessarily high manual review rate or the failure to detect clinically significant abnormalities.

There remains a need in the art for a simple, rapid, method for determining both a comprehensive five-part differential, as well as an extended leukocyte differential, in a single analysis on either a multiparametric high throughput hematology analyzer or a specialty hematology analyzer.

SUMMARY OF THE INVENTION

In one aspect, the present invention provides a composition containing a first antibody, at least one additional antibody, and a third component. These three components are provided for admixture into a single reaction mixture with a biological sample. The first antibody binds to an antigenic determinant that is differentially expressed on populations of leukocytes and non-leukocytes, and is labeled with a first fluorochrome. An additional antibody (or additional antibodies) binds to an antigenic determinant that is differentially expressed on populations of mature and immature granulocytes or myeloid cells. The fluorochrome labeling the additional antibody(s) is the same first fluorochrome, or another fluorochrome having an emission spectrum distinguishable from that of the first fluorochrome. In one embodiment, the third component of the composition is a nucleic acid dye. In another embodiment, a third component of the composition is a lytic system. In another embodiment, both a nucleic acid dye and a lytic system are included in the composition.

In still another aspect, the present invention provides a kit containing a composition of the invention and optional instructions for performing an assay using the composition, also as described by the present invention. Use of a composition or kit containing the lytic system alone as the third component permits the enumeration of at least 7 hematologic cell populations in a biological sample. Use of a composition or kit containing the nucleic acid dye (with or without the lytic system) permits the enumeration of at least 8 hematologic cell populations in the sample.

In another aspect, the invention provides a method for the enumeration of hematologic cell populations in a biological sample. The method includes reacting the sample, an above-described first antibody, and at least one above-described additional antibody in a single reaction mixture. The single reaction mixture is then contacted with a third component prior to passing through a flow cytometer. In one embodiment of this method, the third component is a lytic system that can differentially lyse any mature red blood cells present in the sample and conserve the leukocyte populations. In another embodiment of this method, the third component is a nucleic acid dye that has an emission spectrum that overlaps with at least one of the first emission spectra or the additional emission spectra. In still a further embodiment of the method, the third component includes both the nucleic acid dye and the lytic system. In any of these embodiments, the resulting single reaction mixture is then passed through a single flow aperture in a flow hematology analyzer in a single step that measures the mixture for multiple parameters. These parameters may be the same or different and include one or more channels of fluorescence, one or more optical parameters, one or more electrical parameters, and combinations thereof. The populations of hematological cells are then enumerated in the sample by analyzing at least two parameters for each cell population. Use of the method employing the lytic system alone as the third component permits the enumeration of at least 7 hematologic cell populations, and preferably more, in a biological sample. Use of the method employing the nucleic dye (with or without the lytic system) permits the enumeration of at least 8 hematologic cell populations in the sample, and preferably more.

Other aspects and advantages of the present invention are disclosed in the following detailed description thereof.

DETAILED DESCRIPTION OF THE INVENTION

Figure 1A:
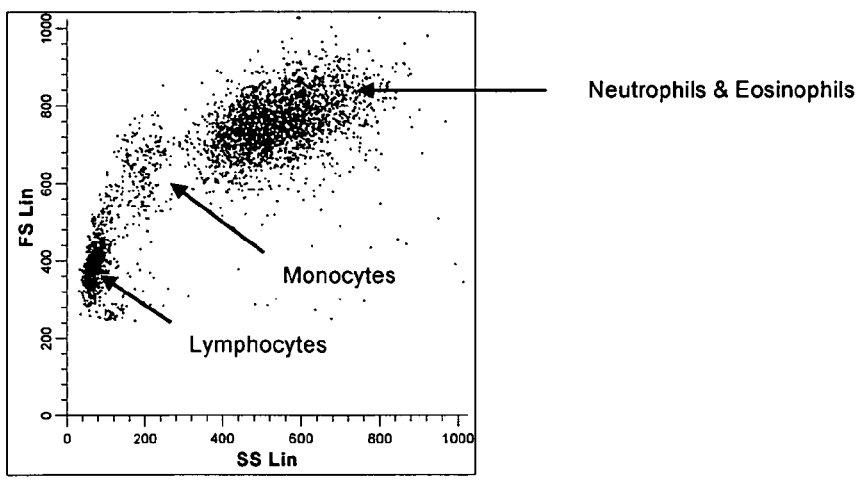
FIG. 1A is a two parameter histogram generated from the experiment described in Example 1 displaying forward light scatter (FS) vs side scatter (SS). At least three cellular populations can be identified and enumerated in this display: lymphocytes, monocytes and granulocytes (containing eosinophils and neutrophils).

The present invention provides methods of performing an automated, rapid, extended leukocyte differential for multiple cell types, e.g., preferably for the five normal leukocyte populations as well as at least two atypical populations. Compositions including the reagents for use in such methods are also provided herein.

In one embodiment, a method for the enumeration of cell populations in a biological sample includes the following steps. A single reaction mixture is formed by rapidly reacting the biological sample with a first antibody labeled with a first fluorochrome having a first emission spectrum. The first antibody binds to an antigenic determinant that is differentially expressed on populations of leukocytes and non-leukocytes in the sample. At least one additional, different antibody that binds to an antigenic determinant that is differentially expressed on populations of mature and immature granulocytes or myeloid cells is added to the reaction mixture. In one embodiment of the method, the additional antibody is labeled with the same first fluorochrome. In another embodiment, the additional antibody is labeled with an additional fluorochrome that has an additional emission spectrum distinguishable from the first emission spectrum of the first fluorochrome. In still additional embodiments of the method, other "additional" antibodies may also be added to the reaction mixture, which antibodies may be labeled with fluorochromes that are the same or have still additional emission spectra from the fluorochromes that label the previously described antibodies. Desirably the method and compositions of this invention employ only 2 or 3 antibodies (i.e., 1 or 2 "additional" antibodies).

According to a method of this invention, the resulting single reaction mixture may be treated with another component. In one embodiment of the method, the additional component is a lytic system that can differentially lyse any red blood cells present in the sample and conserve the leukocyte populations in the sample. A differential lysing of the non-nucleated blood cells in the reaction mixture and an optional quenching of the lysing reaction without altering the intrinsic or extrinsic properties of the nucleated cells, permits retention of the nucleated cells for analysis. In another embodiment of the method, the third component is a nucleic acid dye that has an emission spectrum that overlaps with at least one of the first emission spectra or the additional emission spectra of the fluorochromes labeling the above-noted antibodies. In still another embodiment of this method, both a nucleic acid dye and a lytic system are added to the single reaction mixture.

Following preparation of the reaction mixture, the mixture is passed through a single flow aperture in a multiparametric high throughput flow hematology analyzer in a single analytical step that measures the mixture for multiple parameters. These parameters may be the same or different and include one or more channels of fluorescence, one or more optical parameters, one or more electrical parameters, or combinations thereof. Thereafter, each cell population is identified and enumerated by using at least two of these parameters/cell population.

The final step of the method involves enumerating multiple populations of hematological cells (and optionally some atypical non-hematological cells) in the sample by analyzing at least two parameters for each different cell population. For example, in one embodiment, fluorescence analysis is combined with at least one simultaneously-measured electrical or optical measurement made on each individual cell as it passes through the transducer to identify a cell population. In this manner, an extended differential is obtained without the need for further separation of the lysed and unlysed fractions, if present, in the sample, or for correlation of different measurements made on different cells in the sample in different transducers.

Thus, the method of this invention uses monoclonal antibodies and nucleic acid dyes in an unusual application, i.e., by choosing combinations of dyes and labeled antibodies that have overlapping emission spectra, and thereby creating new "footprints" that permit identification of multiple cell types with a minimum use of reagents and hardware.

The various embodiments of the methods of this invention and the compositions useful therein are described in detail below.

A. The Biological Sample

According to this invention, a biological sample is any mammalian cell-containing suspension that contains leukocytes. Such a specimen or sample can include hematological cells and non-hematological cells. Such a sample includes, without limitation, whole blood, peripheral blood, bone marrow aspirate, lymph node tissue, splenic tissue, cerebrospinal fluid, skin tissue, mucosal tissue, thoracentesis fluids, pleural fluids, and spinal fluid. Hematological cell populations are selected from the group consisting of monocytes, lymphocytes, neutrophils, eosinophils, basophils, myelocytes, metamyelocytes, promyelocytes, immature granulocytes, bands, blast cells, variant lymphocytes and atypical lymphocytes. Non-leukocyte hematological cell populations include red blood cells, nucleated red blood cells, platelets and megakaryocytes. In the blood, atypical cells include myelocytes, metamyelocytes, promyelocytes, immature granulocytes, band cells, blast cells, atypical lymphocytes, variant lymphocytes nucleated red blood cells, giant platelets, plasma cells, etc. Non-hematological cells include epithelial cells and endothelial cells, among others.

Preferably, the biological sample is human whole blood or peripheral blood sample containing the five "normal" leukocyte populations, which are monocytes, lymphocytes, neutrophils, eosinophils, and basophils, as well as possibly a number of atypical cell populations due to disease, reaction to an adverse environmental stimuli, e.g., a carcinogen, or a result of therapeutic treatment. Thus, suitable samples for analysis by the method of this invention are human patient blood samples, which may likely contain both mature and immature leukocyte cells and non-leukocyte populations, as well as atypical cells. For example, a sample contains blast cells. Another sample contains nucleated red blood cells. As another example, the sample contains immature granulocytes. As another example, the sample contains atypical lymphocytes. Other combinations of cells in abnormal samples may also be analyzed by the methods and compositions of this invention.

By applying the method of this invention to such biological samples, information that contributes to the diagnosis, prognosis, staging and treatment of a variety of diseases can be made based on the "extended" or "5+ part" differential of the sample. Desirably, the method of the invention provides a 6-part differential, 7-part differential, 8-part differential, 9-part differential, or 10-part differential. A differential of more than 10 cell populations may also result from application of the methods of this invention, depending on the selection of the components of the single reaction mixture, as indicated above, and on the nature of the sample, e.g., blood, bone marrow, etc.

For use in the method of this invention, the biological sample volumes can be altered to fit the requirements of the system, but preferably range from about 10 µL to about 150 µL.

B. Compositions of the Invention/Components of the Methods

1. Antibodies

The fluorescence signals provided by the antibodies useful in the compositions of this invention, in conjunction with at least one other parametric measurement, provide the data required for a comprehensive extended cell differential in a single analytical process. The composition of reagents, which with the sample form a single reaction mixture, is designed so that no more than two or three antibodies (directed at two or three qualitatively different antigenic determinants) may be utilized without incorporating additional hardware (lasers, photomultiplier tubes, etc.) or more than two fluorochrome labels. It is also designed so that the individual antibody specificities within the composition, in conjunction with each other as well as the electrical or light scatter parameters, are able to provide the most information in a single analysis.

Thus, the compositions useful in the method of this invention desirably contain at least two antibodies that are capable of providing information which differentiates among more than two antigenic determinants present on the cells in the sample. In one embodiment, this differentiation is enabled by using no more than one or two fluorochromes with either the same emission spectra or different emission spectra. In one embodiment, at least two antibodies are utilized according to the present invention labeled with the same fluorochrome. In another embodiment, at least two antibodies are utilized according to the present invention labeled with different fluorochromes. In another embodiment, at least three antibodies are utilized according to the present invention, each labeled with different or the same fluorochromes as at least one of the other antibodies.

The term "antibody" as used herein is intended to encompass a polyclonal, monoclonal, synthetic or recombinant antibody of classes IgG, IgM, IgA, IgD and IgE. Antibody fragments are also useful, including without limitation, a Fab fragment, a Fab' fragment, a F(ab')2 fragment or an Fc antibody fragment of one or more of the above intact antibodies. Similarly a single chain variable antibody fragment or a recombinant construct comprising a complementarity determining region (CDR) of an antibody may be employed as the antibodies useful in these methods. Further, a synthetic antibody or chimeric antibody or humanized antibody construct which shares sufficient CDRs to retain functionally equivalent binding characteristics of an antibody that binds a desired cell surface antigen may also be employed as the antibody of choice. Preferably highly specific antibodies are used in this method.

The individual antibodies for use within the reaction mixture are chosen so that a particular combination in conjunction with light scatter and/or electrical parameters provides the desired extended differential information. Among the antibodies that may be employed in this method are at least one "first" antibody that binds to an antigenic determinant that is differentially expressed on populations of leukocytes and non-leukocytes. Such an antigenic determinant may be completely absent from non-leukocytes and expressed only on leukocytes. Alternatively, such an antigenic determinant may be abundantly expressed on leukocytes and minimally expressed on non-leukocytes. Such an antibody thus permits the identification and differentiation of white blood cells from non-white blood cells, such as RBC, nucleated red blood cells or platelets. In a preferred embodiment, the first antibody is also capable of differentiating between mature leukocytes and immature leukocytes, based on differential expression of the antigenic determinant on leukocytes as they mature and age.

The most desirable antibody for this purpose is anti-CD45. The CD45 antigen is expressed by, or present on, most cells in the leukocyte populations, but is not expressed, or only minimally expressed, if at all, on other hematopoietic cells, such as erythrocytes and megakaryocytes. Differential expression can be displayed within leukocyte populations so that lymphocytes exhibit relatively high expression, whereas basophils exhibit relatively low expression. Expression of the CD45 antigen can also vary as a function of leukocyte maturation level. For example, blasts or stem cells express less CD45 antigen than their mature counterparts. Other antibodies with similar differential binding expression between white cells, non-white cells, and blasts, including anti-CD11a, anti-CD50, anti-CD18, anti-CD53, and anti-CD62L, among others, may be used as the first antibody in the compositions and methods described herein. Also useful are anti-CD235a to glycophorin A, anti-CD235b, anti-CD236, anti-CD236r, anti-CD239, anti-CD 240, anti-CD241 and anti-CD242. Still other useful first antibodies may include anti-CD48, anti-CD82, anti-CD235c and anti-CD36.

The "additional" antibody forming part of the single reaction mixture or part of the composition includes one or more antibodies that bind to an antigenic determinant that is differentially expressed on populations of mature and immature granulocytes or myeloid cells. For example, the distribution of the CD16 antigen is more restricted than CD45 with regard to leukocyte expression. The CD16 antigen has two isoforms: CD16α and CD16β. CD16β is expressed strongly on segmented neutrophils and bands and poorly or not at all on other cells in the myeloid series. In contrast, CD16α is expressed on a subset of leukocytes classified as natural killer (NK) cells, and on monocytes and macrophages. An antibody with broad expression for the CD16 epitope (CD16α and CD16β) is expressed strongly on segmented neutrophils, bands, NK cells, monocytes, and macrophages and expressed poorly or not at all on other cells in the myeloid series. Therefore, in conjunction with anti-CD45 and the additional optical and electrical parameters as selected by this method, the fluorescence of the one or more additional antibodies can identify and distinguish between differentiated myeloid cells, immature myeloid precursors, and stem cells or blasts. For example, because the CD16 antigen may be more conserved than the intrinsic properties of neutrophils, anti-CD16 can also be used to identify degranulated(ing) neutrophils, such as may occur due to age, therapeutic treatments and certain hypogranular conditions. In addition, NK cells can be identified. Other antibodies with useful binding properties that distinguish mature and immature myeloid cells for use as the one or more "additional" antibody in the method or composition include, without limitation, antibodies to CD11b, CD15, CD24, CD35, CD10, CD49d, CD64 and CD87.

Additional antibodies which may be employed in the composition or reaction mixture are those, which desirably bind to, or react specifically with, a different cell surface determinant on another WBC. For example, the CD19 antigen is a B lymphocyte-specific antigen that is expressed on cells of the B lineage from immature pre-B cells to mature B lymphocytes. It is the classical epitope that defines a B cell. The antibody anti-CD19 binds to immature and mature B cells and can be used to differentiate blasts of B cell origin, and permits the identification of such blast cells separately from other WBCs identified by the binding of CD45. Atypical WBCs include immature granulocytes, blasts, band cells and atypical lymphocytes. Antibodies that bind to cell determinants specific for such atypical cells include CD34, which binds to blasts and CD117, etc. The use of these additional antibodies permits further identification and distinction among the atypical cell types.

2. Fluorochromes

Preferably, each antibody selected for use in the composition or method of this invention is associated with, or conjugated to, a fluorescent detectable label, called a fluorochrome. Fluorochromes are commonly used in diagnostic assays. Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP. Alexa dyes, which are not tandem dyes, are also useful. Combinations of such labels, such as Texas Red and rhodamine, FITC+PE, FITC+PECy5, and PE+PECy7, among others may be used depending upon the type of laser employed in the flow cytometry apparatus. Any fluorochrome may be employed, including those excitable by radiation in the red, blue or green wavelengths or combinations thereof. Multiple fluorochromes may be independently selected from available fluorochromes. Alternatively, indirect labeling methods, such as biotin-avidin or primary and secondary labeled antibodies are useful to accomplish a similar effect.

All of these fluorescent dyes are commercially available, and their uses known to the art. Still other fluorescent dyes may be available from other sources or may be developed in the future. Such dyes are anticipated to be useful in the method of this invention in the same manner as is the exemplary fluorescent dye of the examples below. According to one embodiment of this invention, only one fluorochrome is employed to label both the first antibody and at least one additional antibody. According to another embodiment of this invention, two fluorochromes are used. In one aspect, if two fluorochromes are used, each has a differentially detectable emission spectrum, e.g., PE and PECy7, etc. In another aspect, if two fluorochromes are used, each has an overlapping emission spectrum. Selected coupled fluorochromes for use in this invention (using one or two lasers) include PE+PECy5, PE+APC, FITC+PE, APC+PECy7, and PE+PECy7. In still other embodiments, the peak emission spectra of the fluorochrome label(s) used in the composition and method may overlap the peak emission spectra of the nucleic acid dye, if so utilized, as described below.

Methods for coupling or associating the label with the antibody are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995); U.S. Pat. Nos. 6,692,968 and 5,164,311, among others. Thus, selection of the fluorochrome label(s) and coupling methods do not limit this invention.

Optimal concentrations of antibodies used in the method of this invention are defined based upon label selected, desired staining intensity, reaction kinetics and fluorescence carryover between fluorescence channels when using multiple antibodies with only one or two fluorochrome labels. Such concentrations may be determined by the person of skill in the art given the present teachings of this invention.

3. The Optional Nucleic Acid Dye

In certain embodiments of the compositions and methods of this invention, a nucleic acid dye or cytophillic dye is included. The nucleic acid dye useful in this invention has an emission spectrum that overlaps with at least one of the emission spectra of the fluorochromes labeling the first antibody or an additional antibody in the composition or method. In one embodiment the emission spectrum of the nucleic acid dye overlaps multiple fluorochromes useful in these compositions and methods of the invention.

In one embodiment, the nucleic acid dye is a cell-permeant dye. By the term "cell permeant" is meant to describe a dye that readily penetrates a cell membrane and stains the components of the cell without requiring the additional presence of a permeabilizing agent in the composition or reaction mixture. Typically, cell-permeant dyes are utilized to stain live cells or components of cells that have not been lysed.

In another embodiment, the nucleic acid dye is a cell-impermeant dye, such as those cell-impermeant dyes within the red, green or blue-excited wavelength regions.

In a further embodiment, the nucleic acid dye is an intercalating dye or a metachromatic dye. See, for example, the metachromatic dyes noted in Urban et al., 2000 *Acta. Histochem.* 102:259-272.

In a further embodiment, the nucleic acid dye is a non-metachromatic dye. The term "non-metachromatic dye" is meant to describe a fluorescent dye that provides a single wavelength of excitation and/or emission when irradiated at a predetermined wavelength.

Examples of nucleic acid dyes that can be utilized in the present invention include, without limitation, the Pyronin Y dye, acridine dyes such as the Acridine Orange dye, the nonyl Acridine Orange dye (3,6-Bis-(dimethylamino)-10-nonylacridinium bromide, Molecular Probes, Eugene, Oreg.), and the Acridine Red dye (also commercially available as Pyronin B, Sigma-Aldrich Corp., St. Louis, Mo.); the Thiazole Orange dye (Becton Dickinson, Franklin Lakes, N.J.); Propidium Iodide (3,8-Diamino-5-(3-diethylaminopropyl)-6-phenyl-phenanthridinium iodide methiodide, Sigma-Aldrich Corp., St. Louis, Mo.); Ethidium Bromide (Sigma-Aldrich Corp., St. Louis, Mo.); Hexidium Iodide (Molecular Probes, Eugene, Oreg.); Dihydroethidium (Molecular Probes, Eugene, Oreg.); Ethidium Monoazide (Molecular Probes, Eugene, Oreg.), the Toluidine Blue dye (2-Amino-7-dimethylamino-3-methylphenothiazinium chloride, Sigma-Aldrich Corp., St. Louis, Mo.); the TOPRO-3 dye; the YOPRO-1 dye; the SYTO™ dye such as the SYTO™ 17 dye and the SYTO™ 59 dye through SYTO™ 64 dye; the TOTO™ dye such as the TOTO-1 dye and the TOTO-3 dye; the PO-PRO-3 dye; the YOYO™ dye such as the YOYO-1 dye; the BOBO™ dye; the POPO™ dye such as the POPO-3 dye; xanthene dyes; carbocyanine dyes; polymethine dyes including Astra Violet FR; Thiofalvine T; pseudoisocyanine; oxacarbocyanine dyes; azine dyes; diphenylmethane dyes; methine dyes; oxazine dyes; cyanine dyes; styryl dyes; and hydrosystilbamidine (Molecular Probes, Eugene, Oreg.). Many of these dyes, as well as others that can be utilized in the present invention, are commercially available from Molecular Probes Inc. (Eugene, Oreg.). See, U.S. Pat. No. 5,563,070, which is hereby incorporated by reference.

Examples of non-metachromatic dyes include, without limitation, the Neutral Red dye (3-Amino-7-dimethylamino-2-methylphenazine hydrochloride, Sigma-Aldrich Corp., St. Louis, Mo.), the Basic Orange™ 21 dye (Sigma-Aldrich Corp., St. Louis, Mo.), the DiOC dye (1,1'-Dimethyloxacarbocyanine, Molecular Probes, Eugene, Oreg.), the Pyronin™ Y dye (Polysciences, Inc., Warrington, Pa.), the Methylene Blue™ dye (3-Bis-(dimethylamino)-phenothiazin-5-ium chloride, Molecular Probes, Eugene, Oreg.), the Auramine™ O dye (4,4'-(Imidocarbonyl)-bis-(N,N,-dimethylaniline) monohydrochloride, Sigma-Aldrich Corp., St. Louis, Mo.), the LDS™ 751 dye (Quinolinium, 6-(Dimethylamino)-2-[4-[4-(dimethylamino)phenyl]-1,3-butadienyl]-2-ethyl perchlorate, Molecular Probes, Eugene, Oreg.), the Red series dyes, among others, and combinations thereof. See, e.g., various Beckman Coulter catalogs; The Handbook of Fluorescent Probes and Research Products, $6^{th}$ Ed., R. P. Haugland, Molecular Probes, Eugene, Oreg. It should be noted that certain dyes can be metachromatic in some circumstances and non-metachromatic in others.

In one embodiment of the compositions and methods of this invention, the nucleic acid dye is Acridine Orange or nonyl Acridine Orange. In another embodiment, the dye is Thiazole Orange. In still another embodiment the dye is Propidium Iodide. In another embodiment, the dye is Acridine Red or Toluidine Blue dye.

One of skill in the art should be readily able to select the appropriate dye for use in these compositions and methods in view of the additional teachings contained herein.

4. The Optional Lytic System

An optional lytic system can be employed to differentially lyse non-nucleated red blood cells in the biological sample, while conserving the desired intrinsic and extrinsic properties of the leukocyte populations, and conserving nucleated red blood cells (NRBC) as well. In one embodiment, the lytic system is a component of the method or composition in the absence of a nucleic acid dye. In another embodiment, the lytic system is employed in the presence of a nucleic dye, typically where the nucleic acid dye is an impermeant dye, as described above. In some embodiments, a lytic system can include a single lysis reagent. In other embodiments, the lytic system includes a quench step and reagents for same. In some embodiments, a lytic system can include a fixation step and reagents for same.

The lytic system can be a lytic reagent system including, but not limited to: Erythrolyse II (Beckman Coulter, Inc.), the lysing reagent disclosed in U.S. Pat. No. 5,882,933, incorporated by reference for the purposes of identifying the reagents. The lytic reagent can vary with the primary requirements being efficient lysis of the red blood cells, and the conservation of the antigenic determinants and desired electrical and optical properties on the WBCs and NRBCs and desired atypical cells.

In addition to employing a single reagent for lysis, the lytic systems useful in the present invention can include a second reagent, e.g., one that quenches or retards the effect of the lytic reagent during the remaining steps of the method, e.g., while the sample flows through the aperture in the transducer module. A useful lysis retarding agent may be selected depending upon the lysis agent and may likely be employed only where speed is an issue. An example of such a lysis regarding agent is Stabilyse™ reagent (Beckman Coulter, Inc.). The lysis retarding reagent can vary provided that the primary requirement of quenching of the lytic reaction as well as the conservation of the antigenic determinants and desired electrical and optical properties on the cells of interest are accomplished.

A conventional fixation reagent may also be employed depending upon the choice of lytic reagents or the preferred implementation of the method.

Other lytic systems are marketed commercially and include the Immunoprep™ system (Beckman Coulter, Inc.), the Versalyse™ system, the FACSlyse™ system (Bectin Dickenson), or an ammonium chloride system.

5. Other Optional Components

Sphering agents can optionally be included in the composition, reaction mixtures and methods of the invention and can be readily selected by one of skill in the art. Desirably, the sphering reagent is a zwitterionic surfactant which isovolumetrically spheres the red blood cells and reticulocytes and increases permeability. Such reagents can also act as surfactants. Examples of sphering agents include the non-ionic surfactant Dodecyl-β-D-Maltoside, which suitably is in solution with a buffer such as phosphate buffered saline, zwitterionic agents such as alkyl amido betaine or an alkyl betaine such as lauroamidopropylbetaine, cocoamidopropylbetaine and cocoamidosulfobetaine, N-tetradecyl-N,N-dimethyl-3-ammonio-1-propanesulfonate, or N-dodecyl-N,N-dimethyl-3-ammonio-1-propanesulfonate. See, U.S. Pat. Nos. 5,633,167 and 5,438,003, which are hereby incorporated by reference. To effectively isovolumetrically sphere the reticulocytes and red blood cells within a blood sample, the concentration of the sphering reagent in the composition is most preferably from about 3 μg/ml to about 50 μg/ml with a mOsm in the range of about 200 to about 400 mOsm, and preferably from about 250 mOsm to about 350 mOsm. However, one of skill in the art may readily adjust this concentration and osmolarity as needed or desired to isovolumetrically sphere the cells, taking into consideration the surfactant selected.

Some surfactants and detergents that also permeabilize cells may also be employed in the compositions of the invention. Examples of surfactants include, without limitation, the anionic surfactant ammonium perfluoralkyl carboxylate (commercially available as Fluorad® FC-143 (3M Company, Minneapolis, Minn.)), sodium lauroyl myristoyl lactylate [commercially available as Pationic® 138C (R.I.T.A. Corp, Woodstock, Ill.)), or from the non-ionic surfactants Dodecyl-β-D-maltoside, N,N-bis[3-D-glucon-amidopropyl]cholamide, polyoxypropylene-polyoxyethylene block copolymer, N-tetradecyl-β-D-maltoside, Daconyl-N-methyl-glucamide, n-Dodecyl-β-D-glucopyranoside, n-Decyl-β-D-glucopyranoside, polyethylene glycol ester of stearic acid, ethoxylated cocomonoglyceride, octyphenoxypoly(ethyleneoxy)ethanol, ethoxylated octylphenol, and linear alcohol, or, from among the cationic surfactants, coco hydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-dodecyl-N,N-dimethyl-3-ammonio-1-propanesulfonate, N-tetradecyl-N,N-dimethyl-3-ammonio-1-propanesulfonate. Examples of detergents include, without limitation, non-ionic detergents.

Other cell permeabilizing agents can also be included in the compositions of the invention to permit cell impermeant dyes to permeate the cell membrane. Desirably, these components are used at a concentration between about 0 to about 1% of the total composition.

The composition of the invention may further contain other components, such as buffers. Suitable buffers include those that maintain the pH of the composition in the range of about 6 to about 9. Desirably, a pH in the range of about 7 to about 7.5 is maintained in the composition. Additionally, such buffers may also be used to adjust the concentration of one or more of the components of the composition of this invention. Examples of buffers that can be utilized in the present invention include, without limitation, phosphate buffered saline or isotonic saline, such as ISOTON II, Coulter Corporation, Miami, Fla., or the like. See, U.S. Pat. No. 3,962,125, which is hereby incorporated by reference. Selection of an appropriate buffer is not a limitation on the present invention.

Preservatives can also be added to the compositions of the invention, and may be selected from, but not limited to, 5-Chloro-2-methyl-4-isothiazolin-3-one, and 2-methyl-4-isothiazolin-3-one (such preservatives may be purchased commercially, e.g., as ProClin 300 or ProClin 150).

One of skill in the art would be able to select further reagents that can be utilized in the compositions for use in the present invention.

6. Specific Embodiments

The compositions of the invention are typically prepared in an appropriate manner. In one embodiment, all of the components of the reaction mixture other than the sample itself may be assembled to form a kit.

One such composition contains a first antibody meeting the description above and labeled with a first fluorochrome, e.g., anti-CD45PECy7; a second antibody meeting the "additional antibody" description above and labeled with a first fluorochrome, e.g., anti-CD16PECy7; and a nucleic acid dye, e.g., Acridine Orange. This composition in the form of a kit may also contain suitable packaging, glassware or container components and instructions for carrying out the methods of the invention, among other items conventional to a kit. A composition containing these components is designed for admixture into a single reaction mixture with a biological sample, said mixture permitting the enumeration of at least eight or more hematologic cell populations in the sample.

In another embodiment, a composition of the invention contains a first antibody meeting the description above and labeled with a first fluorochrome, e.g., anti-CD45PECy7; a second antibody meeting the "additional antibody" description above and labeled with a first fluorochrome, e.g., anti-CD16PECy7; and a lytic system containing a lysing and quenching reagent. Similar kit components may be included, as described above. A composition containing these components is designed for admixture into a single reaction mixture with a biological sample, said mixture permitting the enumeration of at least seven or more hematologic cell populations in said sample.

In yet another embodiment, a composition of the invention contains a first antibody meeting the description above and labeled with a first fluorochrome, e.g., anti-CD45PECy7; a second antibody meeting the "additional antibody" description above and labeled with a first fluorochrome, e.g., anti-CD16PECy7; a lytic system containing a lysing and quenching reagent, and a nucleic acid dye, e.g., Acridine Orange. Similar kit components may be included, as described above.

In another embodiment a composition contains a first antibody meeting the description above and labeled with a first fluorochrome, e.g., anti-CD45-PECy7; a second antibody meeting the "additional antibody" description above and labeled with a second fluorochrome with a different emission spectrum, e.g., anti-CD16PE; and a nucleic acid dye, e.g., Acridine Orange. This composition, if in the form of a kit may also contain suitable packaging, glassware or container components and instructions for carrying out the methods of this invention, among other items conventional to a kit.

In still another embodiment, a composition of the invention contains a first antibody meeting the description above and labeled with a first fluorochrome, e.g., anti-CD45PECy7; a second antibody, meeting the "additional antibody" description above and labeled with a second fluorochrome, e.g., anti-CD16FITC; and a lytic system containing a lysing and quenching reagent. Similar kit components may be included, as described above.

In yet another embodiment, a composition of the invention contains a first antibody meeting the description above and labeled with a first fluorochrome, e.g., anti-CD45PECy7; a second antibody, meeting the "additional antibody" description above and labeled with a second fluorochrome, e.g., anti-CD16-PE; a lytic system containing a lysing and quenching reagent, and a nucleic acid dye, e.g., Acridine Orange. Similar kit components may be included, as described above.

All of these embodiments may contain any of the additional components described above, including more than one additional antibody with the same or different fluorochrome labels, a sphering agent or other components mentioned above.

In still a further aspect, a composition of this invention may be a kit containing as individual components a first antibody that binds to an antigenic determinant that is differentially expressed on populations of leukocytes and non-leukocytes; at least one additional antibody that binds to an antigenic determinant that is differentially expressed on populations of mature and immature granulocytes or myeloid cells; a first fluorochrome having a first emission spectrum for association with the first antibody and optionally with at least one additional antibody; an additional fluorochrome having an additional emission spectrum distinguishable from said first emission spectrum for association with an additional antibody; and one or more components selected from (1) a lytic system that can differentially lyse any red blood cells present in said sample and conserve the leukocyte populations in a biological sample; or (2) a nucleic acid dye that has an emission spectrum that overlaps with at least one of said first emission spectra or said additional emission spectra, or (3) a combination thereof.

Desirably, packaging for the above components of the composition is included. Alternatively, such a kit further contains one or more sets of instructions for the performance of a method for the enumeration of cell populations in a biological sample, sample and mixing containers, and reagents for labeling said antibodies with said fluorochromes. Still other conventional components of a kit may be readily included.

C. The Multiparametric High Throughput Hematology Methods

According to the present invention, therefore, methods for the rapid identification and analysis of cell populations, both normal and atypical, in a biological sample are performed using the following steps. Preferably, the methods are fully automated, although several steps may be performed manually, if necessary.

1. Method Involving a Single Reaction Mixture and a Lysis System

In one embodiment of a method of the present invention a single reaction mixture is formed by reacting the biological sample, e.g., about 10-200 µL, with the above described "first" antibody, e.g., about 0.1 to about 2 µg. In one embodiment, about 100 µL of sample is used. The binding of this first antibody to leukocytes in the sample is distinguishable from its binding to red blood cells and nucleated red blood cells. At least one above-described "additional" antibody, e.g., about 0.1 to about 2 µg, labeled with either the same fluorochrome on the first antibody or with a second fluorochrome having a distinguishable emission spectrum from that of the first fluorochrome, is introduced into the mixture. The additional antibody permits the identification of different mature and immature granulocytes or myeloid cells. It allows the various types of immature cells to be distinguished from the "normal" or mature white cells. Although in one embodiment, the reaction mixture contains two antibodies, fewer or greater antibodies (i.e., 3) may be employed. For example, as described above, more than one additional antibody directed to an antigenic determinant that permits differentiation between other groups of normal and atypical cells (e.g., mature and immature granulocytes or myeloid cells), with appropriate labels may also be included in the reaction mixture.

The components of the reaction mixture are allowed to react by incubating at room temperature. Generally ambient temperature is employed, although the temperature is not an issue. The incubation/reaction time range is from about 15 seconds to about 15 minutes. The reaction time for the reaction mixture of about 1 minute can be achieved if one adjusts the individual antibody and reagent concentrations, incorporating the use of sphering agents in the formulation and optimizing mixing. This type of rapid reaction time has been demonstrated in the laboratory and is required for an automated high throughput system.

In this embodiment of a method of the invention a lytic system, with one or more reagents is introduced into the reaction mixture. Preferably, this step involves a lyse/quench reaction, which involves contacting a portion of the sample/antibody mixture with a lysing system or lysing reagent, as defined above, for about 4 to 10 seconds. The lytic system differentially lyses any non-nucleated red blood cells present in the sample while conserving the desired intrinsic and extrinsic properties of the leukocyte populations. After several seconds, the effect of the lytic system is then retarded or quenched with a quenching reagent as described and the RBCs are lysed, leaving in the sample, the leukocytes, the atypical cells, if any, and the nucleated RBCs. The quenching reagent generally is in contact with the sample, while the sample flows through the aperture in a cytometry/hematology analyzer. This second reagent is thus in contact with the mixture for at least a few seconds. Volumes of lytic reagent, quench reagent, and fixation reagent, if desired, can be readily selected by the person of skill in the art depending upon the identity of the lysis system used. The incubation of the reaction mixture and subsequent lytic and quenching cycles are preferably fully automated.

The sample containing the antibodies and any of the optional components, with or without lysed RBCs, is then passed through a single flow aperture in a transducer that is capable of making multiple correlated measurements (electrical, fluorescent and optical) on cells as they pass through a single aperture in the transducer module. The transducer thus provides a quantitative analysis of normal leukocytes and at least one (and preferably more than one) subpopulation of atypical leukocytes. As the cells pass through the transducer, multiple correlated electrical, fluorescent and optical measurements are made on each cell. The fluorescence of a cell is preferably measured within discrete, multiple wavelength ranges, which are determined by the respective fluorescence emission spectra of the dyes or fluorochromes used to label the antibodies which bind the cells. In one embodiment, the fluorescence analysis permits the identification of leukocytes from non-leukocytes in the sample, and permits the identification of at least one atypical cell subpopulation.

The optical parameter is generally one of light scatter, e.g., side scatter or forward light scatter. More than one angle of light scatter may be used where only a single fluorochrome is employed. The angle of light scatter may be selected from between about 20 to 70 degrees of light scatter, i.e. medium angle light scatter (MALS); between about 10 to 20 degrees of light scatters, i.e. lower medium angle light scatter (LMALS); between about 20 and about 70 degrees, i.e., upper medium angle light scatter (UMALS) or between about 80-100 degrees of light scatter, nominally orthogonal, i.e. side scatter (SS), low angle forward light scatter between about 2-18 degrees, and axial light loss or absorbance.

The electrical parameter is generally direct current electrical impedance measurement of volume (DC). Alternatively, the electrical parameter can be opacity, which is calculated as the radio frequency of the cell over the DC volume. These parameters are discussed and defined in detail in commonly assigned U.S. Pat. No. 5,125,737, which is incorporated herein by reference.

The above-described flow cytometric steps may be performed manually, partly manually and partly automated, or completely automated. One such automated flow cytometry instrument is described in U.S. Pat. No. 6,228,652, incorporated by reference herein, which discloses an automated instrument by which all of the aforementioned cell characteristics, i.e., DC volume, RF conductivity (opacity), light scatter and fluorescence characteristics, can be determined simultaneously, thereby obviating any need to correlate data gathered from separate transducers. The electrical measurements consist of DC (direct current volume/impedance) and RF (radio frequency). The optical measurements include light scattering and fluorescence. The light scatter measurements may consist of multiple angles of scatter collected on each cell to include low, medium and high forward angle measurements as well as right angle (90 degree/side scatter) measurements. The fluorescence measurements are made by collecting the fluorescence emission on two or three photomultiplier tubes or detectors (PMT).

Desirably useful in performing the analysis of the present invention are hematology instruments that measure electrical, optical and fluorescence parameters. See e.g., the instrument described in U.S. Pat. No. 6,228,532, incorporated herein by reference. In an exemplary embodiment, a 532 nm green diode laser is used as the illumination source in a useful flow hematology system. However, for one skilled in the art, lasers with alternative emission lines, e.g., red laser such as 633 nm or 644 nm laser, blue lasers such as a 488 nm laser, can be substituted and the fluorochromes adjusted appropriately. Dyes may be tailored to the laser system.

The resulting data provides the information required to determine an extended leukocyte differential analysis. According to this method, each cell population is identified by at least two parameters, taking advantage of differing patterns of expression detectable in the fluorescence analysis of the fluorescence in the single reaction mixture. For example, the two parameters may be a channel of fluorescence and an optical parameter, such as side scatter. Another two parameters that may be used to identify a cell population may be two channels of fluorescence. Another two parameters that may be used to identify a cell population may be a channel of fluorescence and an electrical parameter, e.g., DC. Another two parameters that may be used to identify a cell population may be an optical parameter, e.g., SS, and an electrical parameter, e.g., DC. Additional combinations of the measurements made on the single reaction mixture are obvious to one of skill in the art, depending upon the particular fluorochromes, dyes, antibodies, optical and electrical parameters used in this method. These analytical steps are desirably incorporated into algorithms in an automated process.

For example, various cell populations can be identified by the following non-exclusive list of parameters, depending upon the variation of the method used, the identity of the fluorochromes, antibodies, dyes, etc.

TABLE 1

| Cell Population Identified | Parameters Used for Analysis |
|---|---|
| Lymphocytes | DC + RLS; Florescence (FL) + SS |
| Monocytes | DC + RLS; SS + FL |
| Granulocytes | DC + RLS; FL + RLS; FL + SS; FL + FL |
| Eosinophils | FL + SS; DC + RLS; FL + FL |
| Basophils | DC + RLS + RF; FL + SS |
| Blasts | FS + FL; SS + FL; DC + FL |
| Immature Granulocytes | SS + FL; DC + FL; FL + FL |
| NRBC | 2 angles FS; FS + FL; FL + FL |
| NK cells | FL + SS; FL + DC; FL + FL |
| Atypical lymphocytes | FL + FL; SS + FL |
| B Cells | DC + FL; SS + FL; FL + FL |
| Non B Cells | SS + FL; DC + FL |
| Blast Cell lineage | FL + DC; FL + SS |
| Platelets | FS + SS; FS + FL |
| Immature Platelets | FS + FL |
| Reticulated RBCs | DC + FL; FS + FL |
| Bands | FL + SS |

In the embodiment of the method described above, this manipulation of the single reaction mixture permits the enumeration of at least seven hematologic cell populations in the sample.

Therefore, in an embodiment in which the first antibody, e.g., anti-CD45 and at least one additional antibody, e.g., anti-CD16, are labeled with the same fluorochrome, in the reaction mixture, after lysis, the various cell populations that can be identified by practice of this invention using the parameters of fluorescence and an optical parameter or electrical parameter, include lymphocytes, monocytes, granulocytes, eosinophils, basophils, blasts, immature granulocytes, and NRBC.

Still other uses of the methods of this invention demonstrate detection of nucleated red blood cells (NRBCs) in a peripheral blood specimen using the correlated multiparametric analysis of the present invention. NRBCs appear intermingled with debris in RLS and Opacity views. Since CD45 is expressed on cells of leukocyte lineage but not erythroid cells, the NRBCs are located within the CD45 negative population. Therefore NRBCs are first segregated from other nucleated cell populations by isolating the CD45 negative events. NRBCs appear as a CD45 negative, low SS population that overlaps debris but excludes other events such as aged or fragile leukocytes with poor CD45 expression. The NRBCs can then be separated from the debris by gating on the CD45 negative low SS events and displaying them in various angles of light scatter or electrical parameter in either single parameter or multiparameter views.

As another example is an embodiment in which the first antibody, e.g., anti-CD45 and at least one additional antibody, e.g., anti-CD16, are labeled with different fluorochromes. In the reaction mixture, after lysis, the various cell populations that can be identified by practice of this invention using the parameters of fluorescence and an optical parameter or electrical parameter include the cells listed above including NK cells.

As another example, in an embodiment in which the first antibody, e.g., anti-CD45 and an additional antibody, e.g., anti-CD16, are labeled with the same fluorochrome, and another additional antibody, e.g., anti-CD19 is labeled with a different fluorochrome having a distinguishable emission spectra in the reaction mixture, after lysis, the various cell populations that can be identified by practice of this invention using the parameters of fluorescence and an optical parameter or electrical parameter, include cells identified above as well as B cells, non-B cells and blast cell lineage.

This embodiment of the present method can differentially identify the five mature leukocyte populations normally found in peripheral blood (lymphocytes, monocytes, granulocytes, eosinophils & basophils), as well as identify hematopoietic cells that lack the expression of CD45, such as cells of the erythroid and megakaryocytic lineages; and identify the most undifferentiated cells, such as stem cells and blasts.

In an embodiment wherein three monoclonal antibodies and two fluorochromes, e.g., anti-CD16 fluorescence in conjunction with anti-CD19 and anti-CD45, conjugated to a different fluorochrome, are employed with the additional "sizing" parameter, the method of this invention identifies B cells, NK cells, and non-B/non-NK (T) cells; identifies and subcategorizes blasts into at least two groups (B lymphoblasts and non-B lymphoblasts), categorizes benign lymphoproliferative processes into B, NK and non-B/NK processes; identifies and distinguishes between B cell chronic and B cell acute lymphoproliferative processes; and identifies subsets of atypical lymphocytes that represent acute or chronic B cell neoplasms.

A particular example of this embodiment is described below in Example 1. The single reaction mixture included optimal concentrations of anti-CD45PC5 (Phycoerythrin-Cyanine 5) as the first antibody, and used additional antibodies, anti-CD19PE (Phycoerythrin), anti-CD16PE. A variety of substitutions or additions to the monoclonal cocktail are possible to produce the same or similar sets of data as described in Example 1.

2. Method Involving a Single Reaction Mixture Containing a Nucleic Acid Dye

In another variation of the present invention, a single reaction mixture is formed by reacting the biological sample with the above described "first" antibody and at least one above-described "additional" antibody, labeled with either the same fluorochrome on the first antibody or with a second fluorochrome having a distinguishable emission spectra from that of the first fluorochrome, in the same manner as described in the first method described above.

In this alternative method, an additional component is introduced into the reaction mixture, i.e., a nucleic acid dye (about 10 µL of a 0.5 µg/mL to about 20 µg/mL solution, but lower or higher concentrations are possible if one adjusts the antibody concentrations, blood volumes, incubation and/or mixing times, appropriately). This nucleic acid dye has an emission spectrum the overlaps with at least one of the emission spectrum of the fluorochrome-labeled antibodies in the single reaction mixture. Preferably, the peak emission spectra of the fluorochrome label(s) overlap the peak emission spectra of the cytophillic dye. A feature of this embodiment of the invention is that the dye and fluorochrome conjugated antibodies do not have distinct peak fluorescence emissions. Therefore the fluorescence signals detected in any channel of the detection system are characteristic of either the fluorescence emission of the dye alone, the fluorochrome conjugated antibody(s) alone, or the product of the additive fluorescence of the dye and at least one fluorochrome conjugated antibody(s).

These components of the reaction mixture are permitted to react under the same conditions as described above for the first method embodiment. In this present embodiment, the lysis system may be omitted from the reaction mixture, or it may be added to the reaction mixture as described for the embodiment above. Omission of the lytic system from this method permits the enumeration of non-nucleated cell parameters, such as reticulated RBCs or reticulated RBC hemoglobin or megakaryocytes or platelets, if desired.

The resulting single reaction mixture containing the sample, the antibodies, the nucleic acid dye, with or without lysed RBCs is then passed through a single flow aperture in a transducer that is capable of making multiple correlated measurements (electrical and optical) simultaneously on cells as they pass through a single aperture in the transducer module. The operation of the flow cytometer is as described above, and analysis is then made of the cell populations in the sample based upon use of two of the parameters (fluorescence, optical and electrical) per population, also as described above.

In one embodiment the parameters used for this evaluation include forward and side scattered light and a minimum of at least two channels of fluorescence. The fluorescence emission pattern in each of the collected channels is representative of either the dye alone, the fluorochrome conjugated monoclonal antibody alone, or the spectral addition of the dye and at least one of the fluorochrome conjugated monoclonal antibodies in the reaction mixture. However, the method might also employ the VCS parameters of impedance (DC) and conductivity (RF) along with light scatter and fluorescence measurements. As indicated above, a number of suitable lasers may be employed to excite the fluorescence, including a 488 nm blue argon laser, a green 532 nm laser, or a red laser (633 nm, 635 nm, 640 nm or 644 nm) if the dye is a cytophillic red excitable dye used in combination with antibodies conjugated to red excitable fluorochromes.

In the embodiment of the method described above, this manipulation of the single reaction mixture permits the enumeration of at least eight or more hematologic cell populations in the sample. The collected multiparametric data is then analyzed and two parameters per cell population are employed to identify each cell population. For example, at least one size parameter (FS, SS, or DC) in combination with at least one channel of fluorescence data or alternatively two channels of fluorescence data are used to produce an extended differential analysis. The cell populations that are identified by this method include at least the following populations: lymphocytes, monocytes, neutrophils, eosinophils, basophils, NRBCs, blasts, immature granulocytes, atypical/variant lymphocytes. Additional cell populations that are identifiable using embodiments of the methods of this invention include hematopoietic stem cells, hematagones, blast lineage, myeloid maturity index, RBC maturity index, myeloid to erythroid ratio and fragile white cell fractions, NK cells, bands, etc.

With regard to the specific embodiments described herein and in the examples below, substitutions or additions to the monoclonal antibodies contained in the mixture can be made without affecting the ability to produce the same or similar sets of data. The fluorochromes conjugated to specific antibodies can also be changed so that, e.g., FITC, PE, ECD, or PECy5, are utilized and overlap other portions of the nucleic acid dye emission spectrum. Additionally, the antibodies can have different conjugates so that individual antibodies overlap different portions of the dye emission spectrum. The RBC lytic reagent can also vary with the primary requirement being the conservation of the antigenic determinants on the cells of interest and the conservation of the desired intrinsic properties of the cells of interest. These alterations to the described reagent system can be employed by one who is skilled in the art without compromising the ability to obtain substantially the same results.

As an example, in an embodiment in which the first antibody, e.g., anti-CD45 and at least one additional antibody, e.g., anti-CD16, are labeled with the same fluorochrome, and the nucleic acid dye Acridine Orange is added to the reaction mixture, without lysis, the various cell populations that can be identified by practice of this invention using the parameters of fluorescence and an optical parameter or electrical parameter, include those identified previously, and further including platelets, immature platelets, and reticulated RBCs.

Another example involves an embodiment in which the first antibody, e.g., anti-CD45 and at least one additional antibody, e.g., anti-CD16, are labeled with the same fluorochrome, and the nucleic acid dye Acridine Orange is added to the reaction mixture with the lysis system. The various cell populations that can be identified by practice of this invention using the parameters of fluorescence and an optical parameter or electrical parameter, include lymphocytes, monocytes, granulocytes, eosinophils, basophils, immature granulocytes, blasts, NRBCs, NK cell and atypical or variant lymphocytes.

Another example is an embodiment in which the first antibody, e.g., anti-CD45 and at least one additional antibody, e.g., anti-CD16, are labeled with different fluorochromes, and the nucleic acid dye Acridine Orange is added to the reaction mixture, with the lysis system. The various cell populations that can be identified by practice of this invention using the parameters of fluorescence and an optical parameter or electrical parameter, include lymphocytes, monocytes, granulocytes, eosinophils, basophils, immature granulocytes, blasts, NRBCs, NK cell and atypical or variant lymphocytes, activated monocytes, and bands.

The examples below further illustrate other embodiments of this variation of the method and illustrate the identification of multiple cell populations in the samples. As one of skill in the art can readily determine from the teachings herein, many other variations of these methods can be exemplified by using different fluorescence, optical and electrical parameter pairs and selected antibodies, fluorochromes and dyes, as well as other optional components for the reaction mixtures. These variations are readily apparent from the above descriptions. All variations to the described method are expected to be obvious to the person of skill in the art, based on the disclosure herein and the information known in the art.

This invention therefore demonstrates a minimalist approach in the number of tranducers, hardware, fluorochromes and monoclonal reagents used to perform an extended cell differential in a single analytical process. The method of this invention offers many advantages or improvements over current methods of hematological analysis. Among these advantages are a more robust, extended differential that can include from seven to about 11 cell populations identified in a single reaction mixture. These methods offer more and alternative means for determining the basic differential, i.e., to apply an algorithm to the cell populations, e.g., lymphocytes, monocytes, neutrophils, eosinophils and basophils such as in the illustrated figures referenced herein. This opportunity is particularly important when the significant cells in the biological specimen are in the presence of conditions that may interfere with one particular approach to population determinations. For example, such interfering conditions occur with certain types of chemical interference, age, cell fragility, and/or the presence of atypical cell types that obscure the evaluation of a normal 5-part differential.

The ability to positively identify cells by multiparametric electrical and optical measurements in a single analysis vastly improves the ability to positively identify and select for additional clinically relevant blood cell populations, such as atypical cell types. Such selection eliminates the high false positive or false negative determinations that plague current methods of hematological analysis.

The method of this invention further extends the ability to provide new information that cannot be obtained by the parametric limitations on current hematology analyzers. The automation of these analyses substantially improves the efficiency of the hematology laboratory by eliminating unnecessary labor and more efficiently directing the workflow for further testing and analysis.

EXAMPLES

The following examples illustrate various aspects of the invention. These examples do not limit the scope of this invention that is defined by the appended claims. The following Examples 1-9 employ two antibodies: The first antibody is an antibody to CD45. The CD45 antigen is expressed by most cells in the leukocyte lineage but not expressed on other hematopoietic cells such as erythrocytes and lo megakaryocytes. It is also known to display differential expression within the leukocytes so that lymphocytes exhibit relatively high expression, whereas basophils have lower expression. Expression of the CD45 antigen can also vary as a function of leukocyte maturation level with blasts or stem cells expressing less CD45 antigen than their mature counterparts. Therefore, the combination of AO fluorescence and anti-CD45 fluorescence, in conjunction with light scatter and/or an electrical measurement, such as DC, can be used to (1) differentially identify the leukocyte populations normally found in peripheral blood (lymphocytes, monocytes, granulocytes, eosinophils & basophils) (2) identify hematopietic cells that lack the expression of CD45 such as cells of the erythroid and megakaryocytic lineages (3) and identify the most undifferentiated cells, such as stem cells and blasts.

In contrast, the distribution of the CD16 antigen is more restricted with regard to leukocyte expression. The CD16 antigen has two isoforms, CD16 alpha and CD16 beta. CD16 beta is expressed strongly on segmented neutrophils and bands and poorly or not at all on other leukocytes. CD16 alpha follows a similar pattern of expression except that it is also expressed on a subset of leukocytes classified as natural killer cells and activated monocytes. The method of this invention allows for enhanced separation between neutrophils and eosinophils in a sample that has CD16PC7 added compared to the spatial separation observed in the absence of CD16. This enhanced separation is obtained because mature segmented neutrophils express the CD16 antigen but eosinophils have either less or no CD16 antigen present. Therefore CD16 can be used to enhance the separation in these two populations. The CD16 antigen is also more weakly expressed or absent on immature granulocytes (metamyelocytes, myelocytes and promyelocytes) than on neutrophils.

Therefore, the separation and identification of various nucleated cell populations can be achieved by the addition of CD16 in the method of this invention. The presence of these populations may differ in the views of the different fluorescence channels. The present invention thus provides the ability to have multiple analytical strategies or algorithms for identification and enumeration of the desired cell types.

Therefore in conjunction with AO fluorescence, anti-CD45 fluorescence, light scatter and/or electrical measurements, anti-CD16 fluorescence can identify and distinguish between differentiated myeloid cells, immature myeloid precursors and stem cells or blasts. Because the CD16 antigen may be more conserved than the intrinsic properties of neutrophils, it can also be used to identify degranulated(ing) neutrophils such as may occur due to age, therapeutic treatments and certain hypogranular conditions. In addition, natural killer cells and activated monocytes can be identified.

Example 1

A single reaction mixture was prepared by reacting 100 μL of normal human peripheral blood with about 1 μg of anti-CD45PC7, i.e., a first antibody labeled with a first fluorochrome having a first emission spectrum, said first antibody binding to an antigenic determinant that is differentially expressed on populations of leukocytes and non-leukocytes and about 1 μg of anti-CD16-PC7, i.e., an additional antibody labeled with same fluorochrome having the same emission spectrum. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a nucleic acid stain.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the leukocyte populations. After about 8 seconds, the quenching reagent (Immunoprep™ reagent B; 265 μL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module. This flow cytometry system is capable of measuring 5 channels of fluorescence in combination with side scatter (90 degrees) and forward scatter (2-18 degrees). The system utilizes a blue argon ion laser as an excitation source for the fluorescence detection, although the method can also employ a green laser excitation source and obtain equal or better results.

Figure 1B:
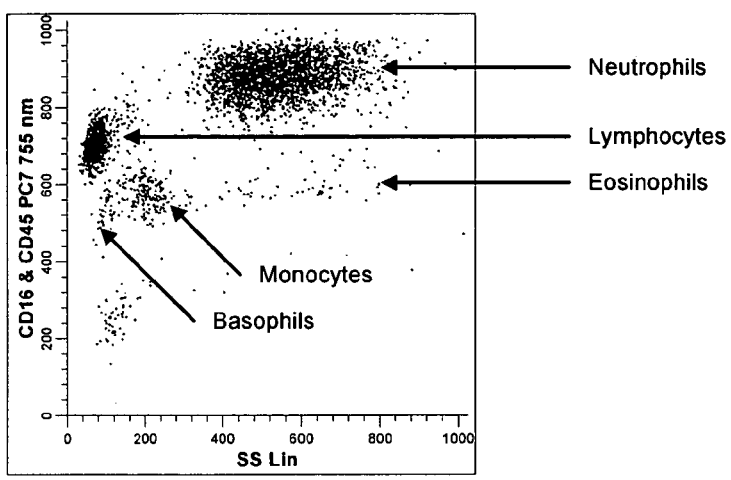
FIG. 1B is a two parameter histogram generated from the same experiment displaying fluorescence of (CD16-PC7 & CD45-PC7) vs side scatter. At least five cellular populations can be identified and enumerated in this display: lymphocytes, monocytes, basophils, eosinophils and neutrophils.
Figure 1C:
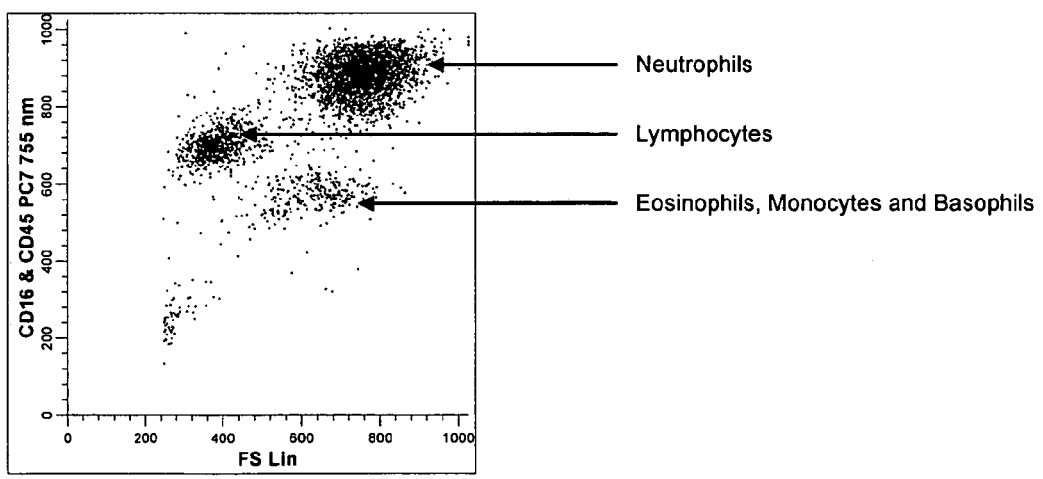
FIG. 1C is a two parameter histogram generated from the same experiment, displaying fluorescence of (CD16-PC7 & CD45-PC7) vs forward scatter. At least three cellular populations can be identified and enumerated in this display: lymphocytes, neutrophils and a third cluster containing eosinophils, monocytes and basophils.

The results of this exemplary hematological analytic process are displayed in dual parameter histograms of FIG. 1A (displaying results of FS+SS, permitting identification of 3 cell populations), FIG. 1B (displaying FL of PC7 vs. SS, permitting identification of 5 cell populations), and FIG. 1C (displaying FL of PC7 vs. FS, permitting identification of 3 cell populations), as described above in figure descriptions. The analysis is performed offline on listmode data files of each acquisition using commercially available software such as RXP or CXP software (Beckman Coulter, Inc.) or Winlist software (Verity Software), or freeware such as WinMD1 software.

More two parameter combinations than are shown can be used in the determination of cell populations. The figures are simplified for ease of presentation as two-dimensional scattergrams. The figures demonstrate that the monoclonal cocktail in conjunction with other optical parameters provide a much more hardy and robust differential. Multiple views are provided by this method in which basophils can be identified. With regard to extended differential cell types, the area where blasts would be expected to appear may be observed in a log CD45 vs SS view. In this dimension, as well as in alternative light scatter dimensions, blasts would not obscure the presence of normal cell types and therefore both the 5-part differential and blast detection/enumeration can be performed. Blasts are sometimes described as atypical lymphocytes upon manual examination. The categorization of cells as atypical lymphocytes is quite broad (blasts, CLLs, reactive and or activated lymphocytes) and this description is usually a signal to initiate further clinical testing. The characterization of blasts demonstrates distinct patterns that differentiate them from other types of cells in the peripheral blood. These include, but are not restricted to, low to no expression of the CD45 antigen, increased light scatter and increased electrical impedance (DC) as compared to normal small lymphocytes. Therefore, blasts that are described morphologically as atypical lymphocytes or any other description can be identified as blasts by the present method. Chronic lymphocytic leukemias are often but not always described morphologically as atypical lymphocytes.

Since immature granulocytes do not express CD16, mature and immature granulocytes can be differentiated from each other as well as other cell types including NK cells and activated monocytes.

Example 2

A single reaction mixture was prepared by reacting 100 μL of normal human peripheral blood with about 1 μg of anti-CD45PE, i.e., a first antibody labeled with a first fluorochrome having a first emission spectrum, said first antibody binding to an antigenic determinant that is differentially expressed on populations of leukocytes and non-leukocytes and about 1 μg of anti-CD16-PC7, i.e., an additional antibody labeled with a second fluorochrome that has an emission spectrum distinguishable from the emission spectrum of the fluorochrome PE. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a nucleic acid stain.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the leukocyte populations. After about 8 seconds, the quenching reagent (Immunoprep™ reagent B; 265 μL) is introduced into the mixture for 10 seconds, to terminate the lytic reaction. No fixation was used.

Thereafter, the mixture is allowed to flow into a transducer module that is capable of making multiple correlated measurements (electrical, fluorescent and optical) on cells as they pass through a single aperture in the transducer module.

Figure 2A:
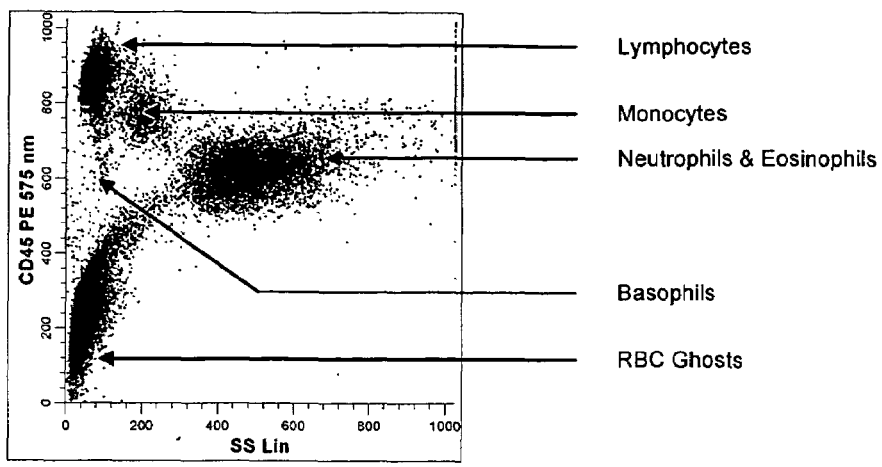
FIG. 2A is a two parameter histogram generated from the experiment described in Example 2, displaying CD45-PE fluorescence vs side scatter (SS). At least four cellular populations are identified and enumerated in this display: lymphocytes, monocytes, basophils and a cluster of granulocytes containing eosinophils and neutrophils.
Figure 2B:
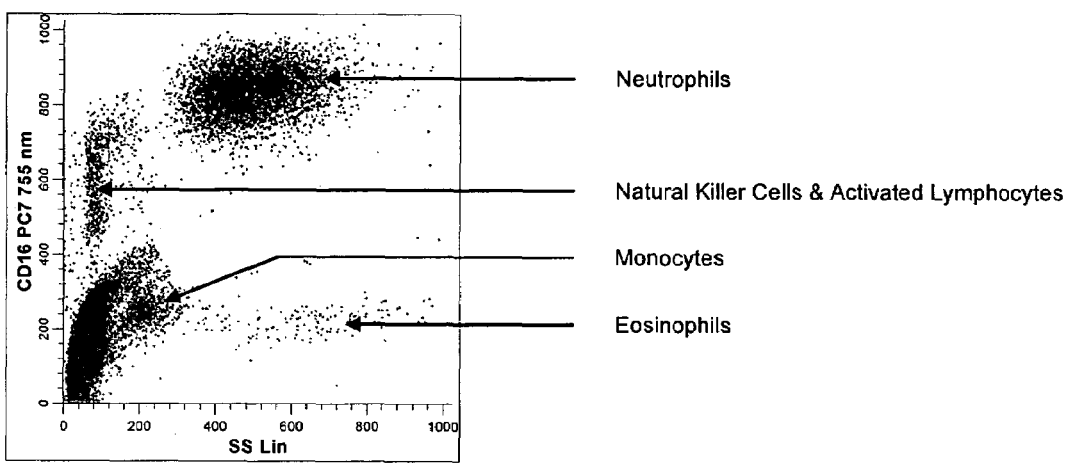
FIG. 2B is a two parameter histogram generated from the experiment described in Example 2, displaying fluorescence of CD16-PC7 vs side scatter (SS). At least four cellular populations are identified and enumerated in this display: neutrophils, monocytes, eosinophils and a cluster containing natural killer cells and activated lymphocytes.
Figure 2C:
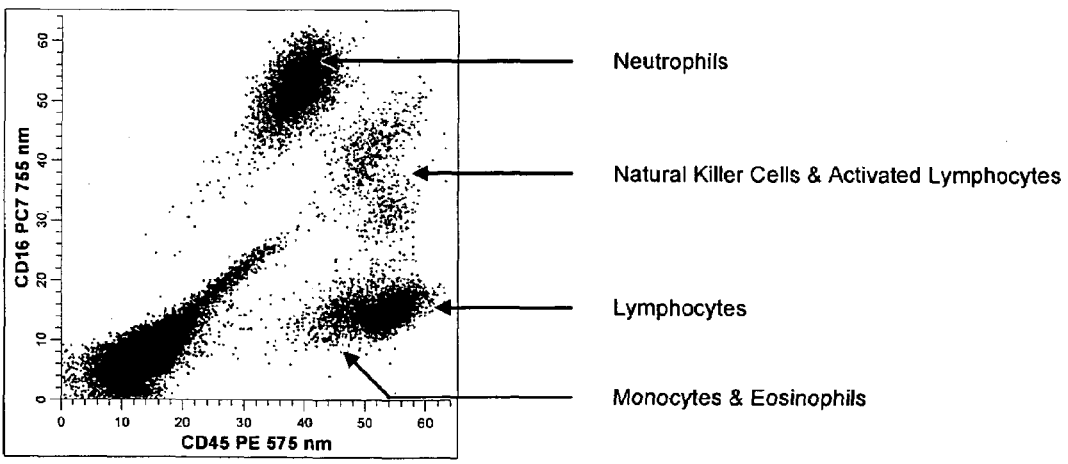
FIG. 2C is a two parameter histogram generated from the experiment described in Example 2, displaying CD16-PC7 fluorescence vs CD45-PE fluorescence. At least four cellular populations are identified and enumerated in this display: lymphocytes, neutrophils, a cluster containing eosinophils and monocytes and an additional cluster containing natural killer cells and activated lymphocytes.

The results of this exemplary hematological analytic process are displayed in the dual parameter histograms of FIGS. 2A thru 2C. FIG. 2A is a two parameter histogram displaying side scatter (SS) vs CD45-PE fluorescence. At least four cellular populations are identified and enumerated in this display: lymphocytes, monocytes, basophils and a cluster of granulocytes containing eosinophils and neutrophils. FIG. 2B is a two parameter histogram displaying fluorescence of CD16-PC7 vs side scatter (SS). At least four cellular populations are identified and enumerated in this display: neutrophils, monocytes, eosinophils and a cluster containing natural killer cells and activated lymphocytes. FIG. 2C is a two parameter histogram displaying CD16-PC7 fluorescence vs CD45-PE fluorescence. At least four cellular populations are identified and enumerated in this display: lymphocytes, neutrophils, a cluster containing eosinophils and monocytes and an additional cluster containing natural killer cells and activated lymphocytes.

Example 3

A single reaction mixture was prepared by reacting 200 µL of normal human peripheral blood with about 1 µg of anti-CD45PC5, i.e., a first antibody labeled with a first fluorochrome having a first emission spectrum, said first antibody binding to an antigenic determinant that is differentially expressed on populations of leukocytes and non-leukocytes and about 1 µg of anti-CD16-PE, i.e., an additional antibody labeled with a second fluorochrome that has an emission spectrum distinguishable from the emission spectrum of the fluorochrome PC5. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a nucleic acid stain.

A portion (about 34 µL) of this reaction mixture is then reacted for about 6 seconds with the lytic system (about 556 µL of the Synlyse system; see U.S. Pat. Nos. 6,573,102 and 5,763,280) that differentially lyses the non-nucleated red blood cells in the blood specimen while conserving the desired intrinsic and extrinsic properties of the leukocyte populations. After about 6 seconds, the quenching reagent (Stabilyse; 240 µL) is introduced into the mixture for 10 seconds, to retard the lytic reaction. No fixation was used.

Thereafter, the mixture is allowed to flow into a transducer module that is capable of making multiple correlated measurements (electrical, fluorescent and optical) on cells as they pass through a single aperture in the transducer module (see U.S. Pat. No. 6,228,652).

Figure 3A:
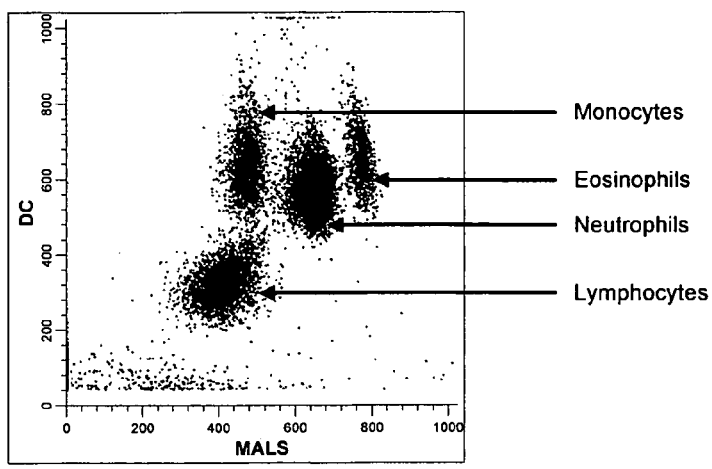
FIG. 3A is a two parameter histogram generated from the experiment described in Example 3, displaying DC (Impedence) vs Median Angle Light Scatter (MALS) which is a forward angle of light scatter from approximately 20 to 40 degrees. At least four cellular populations are identified and enumerated in this display: lymphocytes, monocytes, neutrophils and eosinophils.
Figure 3B:
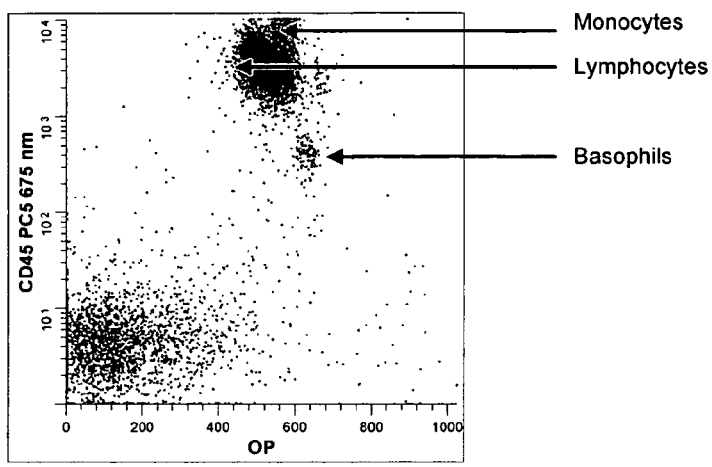
FIG. 3B is a two parameter histogram generated from the experiment described in Example 3, displaying CD45-PC5 fluorescence vs Opacity (OP) where OP=Radio Frequency (RF)/Impedence (DC) following removal of the neutrophils and eosinophils by gating them out from histogram FIG. 3A. In this example three cellular populations are identified and enumerated: lymphocytes, monocytes and basophils.
Figure 3C:
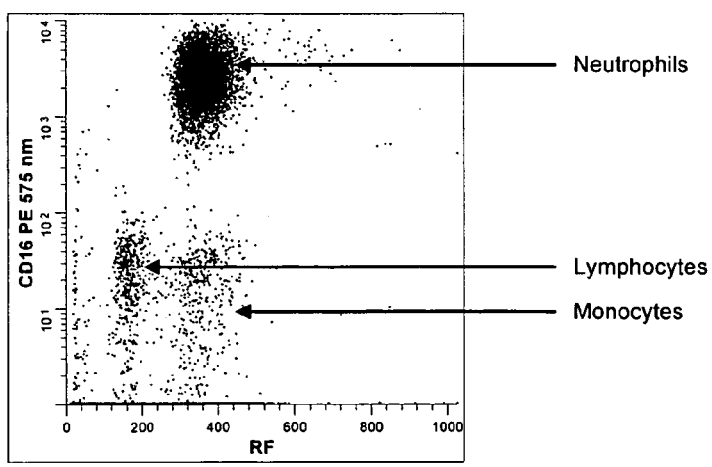
FIG. 3C is a two parameter histogram generated from the experiment described in Example 3, displaying CD16-PE fluorescence vs RF. Three cellular populations are identified and enumerated in this display: lymphocytes, monocytes and neutrophils.

FIGS. 3A thru 3C are dual parameter histograms displaying the results of this experiment. FIG. 3A displays DC (Impedence) vs Median Angle Light Scatter (MALS) which is a forward angle of light scatter from approximately 20 to 40 degrees. At least four cellular populations are identified and enumerated in this display: lymphocytes, monocytes, neutrophils and eosinophils. FIG. 3B displays CD45-PC5 fluorescence vs Opacity (OP) where OP=Radio Frequency (RF)/Impedance (DC) following removal of the neutrophils and eosinophils by gating them out from histogram FIG. 3A. Three cellular populations are identified and enumerated: lymphocytes, monocytes and basophils. FIG. 3C displays CD16-PE fluorescence vs RF. Three cellular populations are identified and enumerated in this display: lymphocytes, monocytes and neutrophils.

Example 4

A single reaction mixture was prepared by reacting 200 µL of a human peripheral blood specimen containing immature granulocytes and bands, with about 1 µg of anti-CD45PC5, i.e., a first antibody labeled with a first fluorochrome having a first emission spectrum, said first antibody binding to an antigenic determinant that is differentially expressed on populations of leukocytes and non-leukocytes and about 1 µg of anti-CD16-PE, i.e., an additional antibody labeled with a second fluorochrome that has an emission spectrum distinguishable from the emission spectrum of the fluorochrome PC5. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a nucleic acid stain.

A portion (about 34 µL) of this reaction mixture is then reacted for about 6 seconds with the lytic system (about 556 µL of the Synlyse system; see U.S. Pat. Nos. 6,573,102 and 5,763,280) that differentially lyses the non-nucleated red blood cells in the blood specimen while conserving the desired intrinsic and extrinsic properties of the leukocyte populations. After about 6 seconds, the quenching reagent (Stabilyse; 240 µL) is introduced into the mixture for 10 seconds, to retard the lytic reaction. No fixation was used.

Thereafter, the mixture is allowed to flow into a transducer module that is capable of making multiple correlated measurements (electrical, fluorescent and optical) on cells as they pass through a single aperture in the transducer module (see U.S. Pat. No. 6,228,652).

Figure 4A:
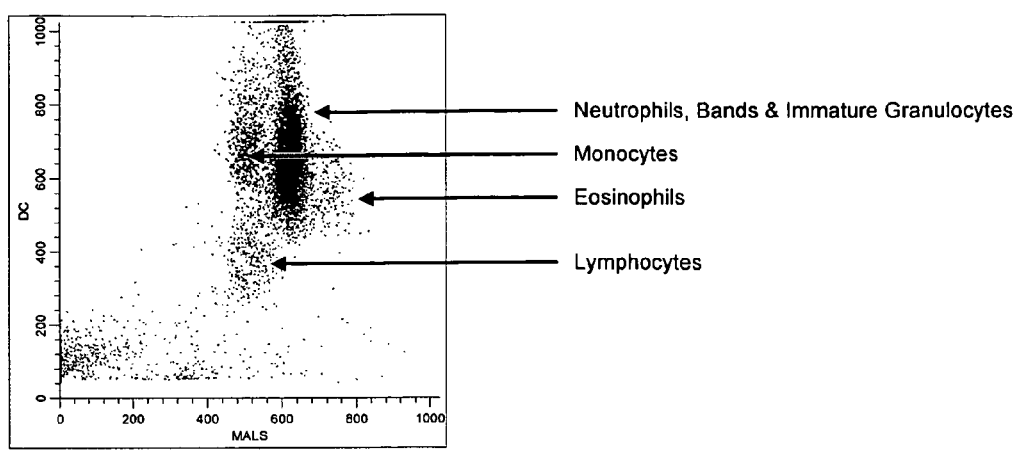
FIG. 4A is a two parameter histogram generated from the experiment described in Example 4, displaying DC (Impedence) vs Median Angle Light Scatter (MALS). At least four cellular populations are identified and enumerated in this display: lymphocytes, monocytes, eosinophils and a cluster containing neutrophils, bands and immature granulocytes.
Figure 4B:
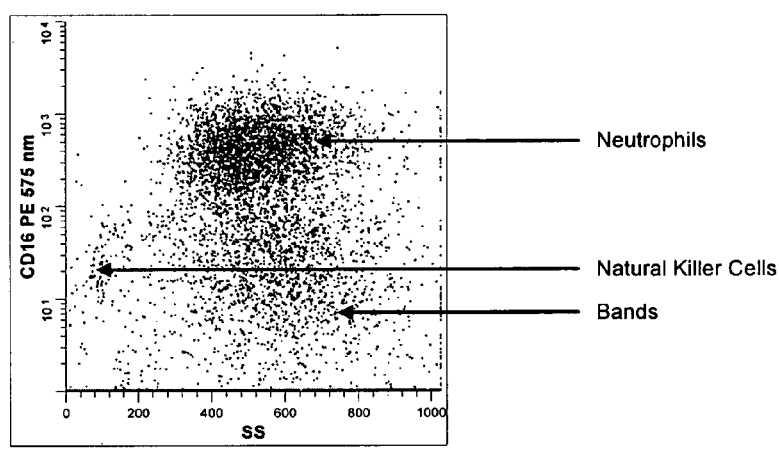
FIG. 4B is a two parameter histogram generated from the experiment described in Example 4, displaying fluorescence of CD16-PE vs SS. In this example at least three cellular populations are identified and enumerated: neutrophils, bands and natural killer cells.
Figure 4C:
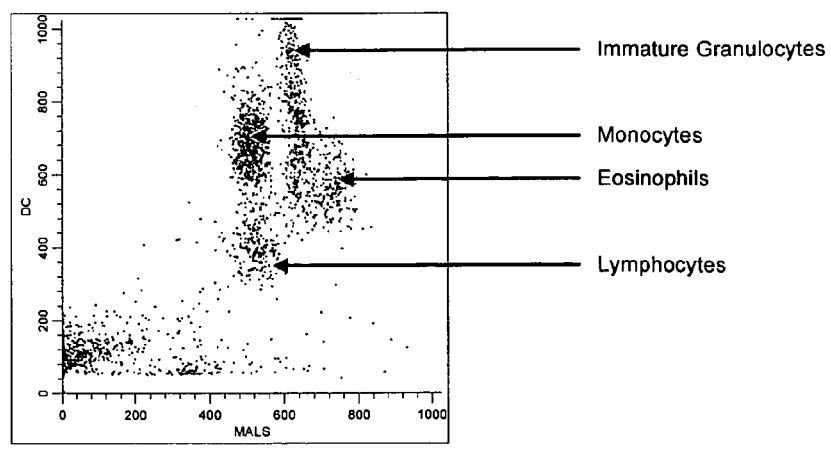
FIG. 4C is a two parameter histogram generated from the experiment described in Example 4, displaying DC vs MALS following removal of the neutrophils and bands by gating them out from the histogram in FIG. 4B. At least four cellular populations are identified and enumerated in this display: lymphocytes, monocytes, eosinophils and immature granulocytes.
Figure 4D:
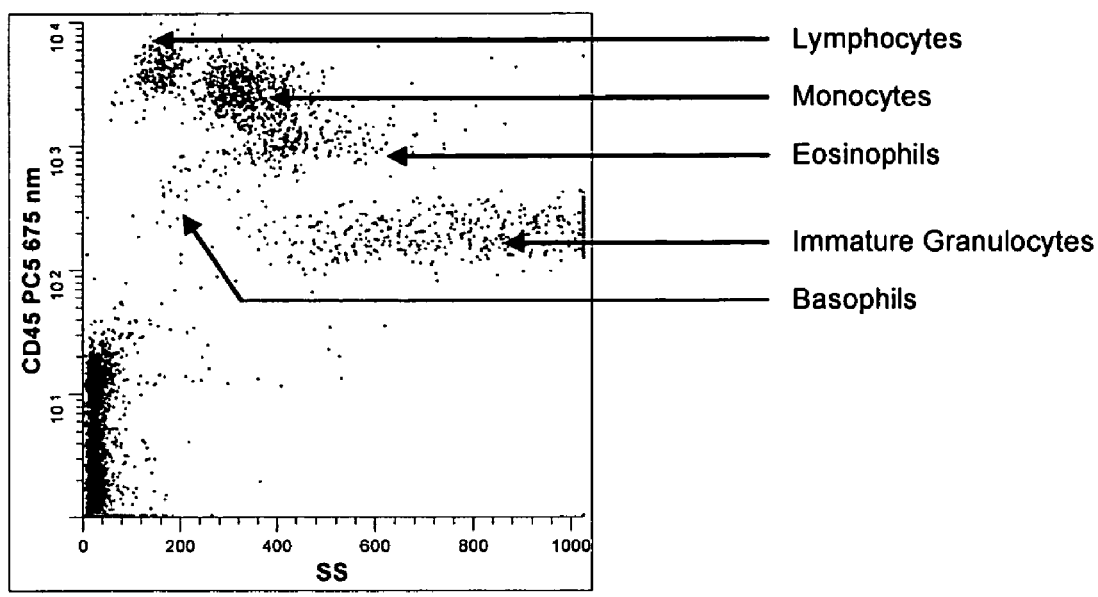
FIG. 4D is a two parameter histogram generated from the experiment described in Example 4, displaying fluorescence of CD45-PC5 vs SS following removal of the neutrophils and bands by gating them out from the histogram in FIG. 4B. At least five cellular populations are identified and enumerated in this display: lymphocytes, monocytes, eosinophils, basophils and immature granulocytes.

FIGS. 4A thru 4D are dual parameter histograms providing an analysis of this sample based on the methods of this invention. FIG. 4A displays DC (Impedence) vs Median Angle Light Scatter (MALS). At least four cellular populations are identified and enumerated in this display: lymphocytes, monocytes, eosinophils and a cluster containing neutrophils, bands and immature granulocytes. FIG. 4B displays fluorescence of CD16-PE vs SS. At least three cellular populations are identified and enumerated: neutrophils, bands and natural killer cells. FIG. 4C displays DC vs MALS following removal of the neutrophils and bands by gating them out from the histogram in FIG. 4B. At least four cellular populations are identified and enumerated in this display: lymphocytes, monocytes, eosinophils and immature granulocytes. FIG. 4D displays fluorescence of CD45-PC5 vs SS following removal of the neutrophils and bands by gating them out from the histogram in FIG. 4B. At least five cellular populations are identified and enumerated in this display: lymphocytes, monocytes, eosinophils, basophils and immature granulocytes.

Example 5

A single reaction mixture was prepared by reacting 100 µL of normal human peripheral blood with about I pg of anti-CD45-PC7, the first antibody, and about 1 µg of anti-CD16-PC7, the additional antibody labeled with the same fluorochrome. The antibody concentrations (about 1 µg each) are optimized based on titration of the individual antibodies. Optimal concentrations were defined based upon desired staining intensity and reaction kinetics. This reaction mixture is mixed briefly and incubated at room temperature for approximately 10 minutes. The reaction mixture was then contacted with a nucleic acid dye (Acridine Orange; approximately 1.25 µg/ml), which has an emission spectrum that overlaps with the emission spectra of PC7. The dye PC7 has a peak emission wavelength of approximately 770 nm when excited with a blue or green laser. In contrast, the Acridine Orange emission spectrum extends from the low 500 nm range to greater than 755 nm when staining subcellular elements in situ (when excited with a blue laser). This is in contrast to the emission of Acridine Orange in solution where the spectral emission is minimal to non-existent at 700 nm.

This mixture was analyzed according to the method of this invention, but without lysing the red blood cells present in the sample. The mixture was allowed to flow into a transducer module that is capable of making multiple correlated measurements (fluorescent and optical) on cells as they pass through a single aperture in the transducer module.

Figure 5A:
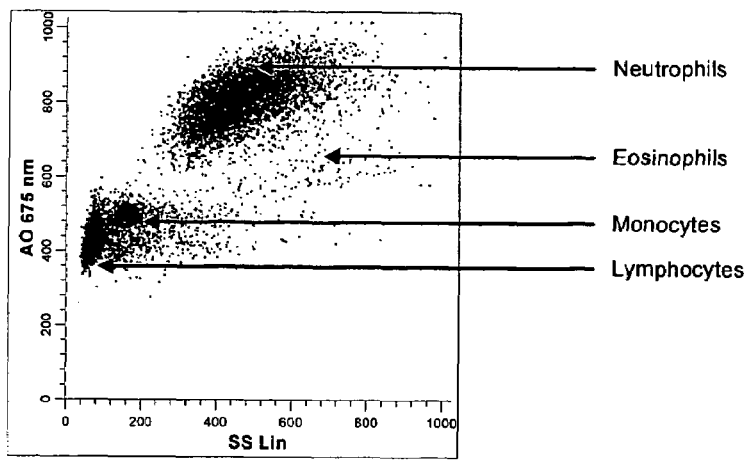
FIG. 5A is a two parameter histogram generated from the experiment described in Example 5, displaying AO fluorescence at a wavelength of approximately 675 nm vs SS. At least four cellular populations are identified and enumerated in this display: lymphocytes, monocytes, eosinophils and neutrophils.
Figure 5B:
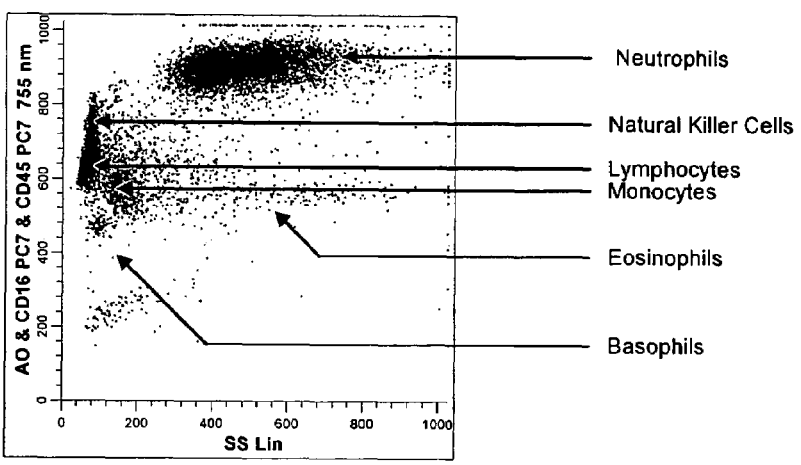
FIG. 5B is a two parameter histogram generated from the experiment described in Example 5, displaying the fluorescence of AO, CD16-PC7 & CD45-PC7 at a wavelength of approximately 755 nm vs SS. At least six cellular populations are identified and enumerated: lymphocytes, monocytes, neutrophils, eosinophils, basophils and natural killer cells.
Figure 5C:
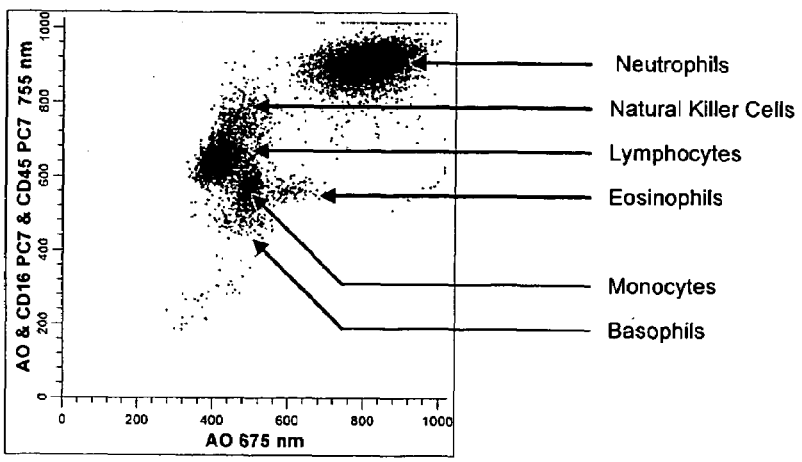
FIG. 5C is a two parameter histogram generated from the experiment described in Example 5, displaying the fluorescence of AO, CD16-PC7 & CD45-PC7 at a wavelength of approximately 755 nm vs the fluorescence of AO at a wavelength of approximately 675 nm. At least six cellular populations are identified and enumerated: lymphocytes, monocytes, neutrophils, eosinophils, basophils and natural killer cells.

FIGS. 5A thru 5C are dual parameter histograms demonstrating the results. The RBCs are not apparent in the histograms since they were purposely set below the electronic threshold of the system in order to emphasize the quantity of white blood cell events collected. FIG. 5A displays AO fluorescence at a wavelength of approximately 675 nm vs SS. At least four cellular populations are identified and enumerated in this display: lymphocytes, monocytes, eosinophils and neutrophils. FIG. 5B displays the fluorescence of AO, CD16-PC7 & CD45-PC7 at a wavelength of approximately 755 nm vs SS. At least six cellular populations are identified and enumerated: lymphocytes, monocytes, neutrophils, eosinophils, basophils and natural killer cells. FIG. 5C displays the fluorescence of AO, CD16-PC7 & CD45-PC7 at a wavelength of approximately 755 nm vs the fluorescence of AO at a wavelength of approximately 675 nm. At least six cellular populations are identified and enumerated: lymphocytes, monocytes, neutrophils, eosinophils, basophils and natural killer cells.

Example 6

A single reaction mixture was prepared by reacting 100 µL of normal human peripheral blood with about 1 µg of anti-CD45-PC7 (the first antibody), and about 1 µg of anti-CD16-PE (the additional antibody labeled with a fluorochrome having a different emission spectrum from that of PC7). The reaction mixture was then contacted with Acridine Orange (approximately 1.25 µg/ml), which has an emission spectrum that overlaps with the emission spectra of PC7 and PE. This reaction mixture is mixed briefly and incubated at room temperature for approximately 10 minutes.

The sample was then passed through a single flow aperture in a flow hematology analyzer without lysing the red blood cells present in the sample. The RBCs are not apparent in the histogram displays as they were set below the electronic threshold of the system in order to maximize the quantity of white blood cell events displayed.

Figure 6A:
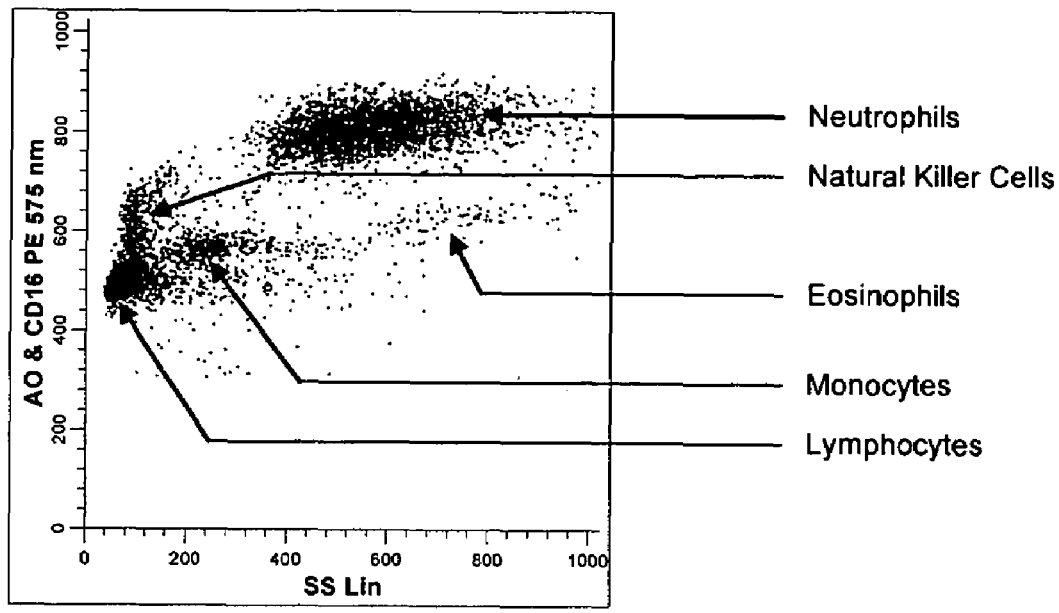
FIG. 6A is a two parameter histogram generated from the experiment described in Example 6, displaying AO and CD16-PE fluorescence at a wavelength of approximately 575 nm vs SS. At least five cellular populations are identified and enumerated in this display: lymphocytes, monocytes, eosinophils, neutrophils and natural killer cells.
Figure 6B:
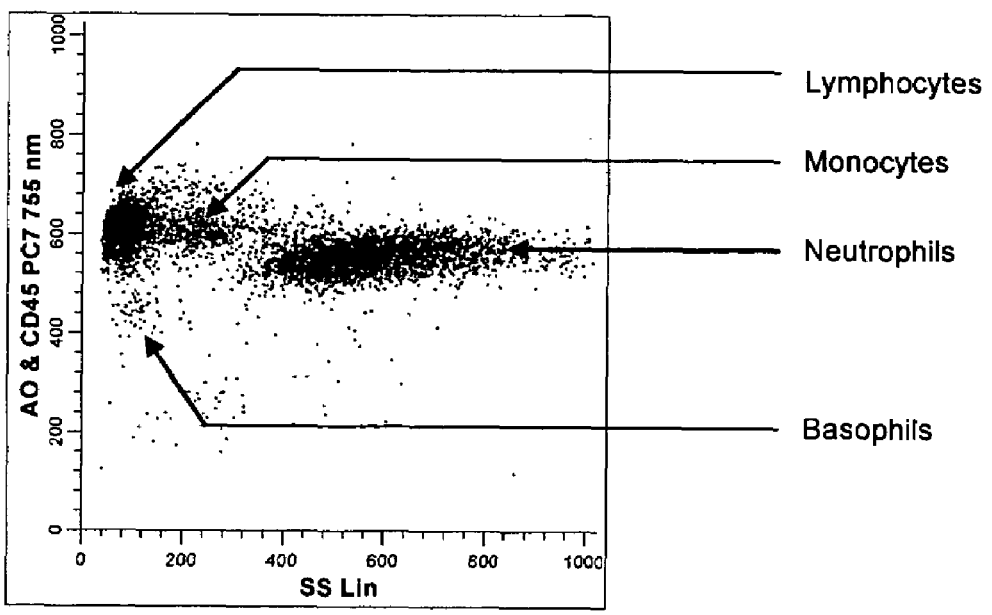
FIG. 6B is a two parameter histogram generated from the experiment described in Example 6, displaying of AO & CD45-PC7 fluorescence at a wavelength of approximately 755 nm vs SS. At least four cellular populations are identified and enumerated: lymphocytes, monocytes, neutrophils, and basophils.

FIGS. 6A and 6B are dual parameter histograms displaying the results of this experiment. FIG. 6A displays AO and CD16-PE fluorescence at a wavelength of approximately 575 nm vs SS. At least five cellular populations are identified and enumerated in this display: lymphocytes, monocytes, eosinophils, neutrophils and natural killer cells. FIG. 6B displays AO & CD45-PC7 fluorescence at a wavelength of approximately 755 nm vs SS. At least four cellular populations are identified and enumerated: lymphocytes, monocytes, neutrophils, and basophils.

Example 7

A single reaction mixture was prepared by reacting 100 µL of an abnormal human peripheral blood specimen with about 1 µg of anti-CD45-PC7, the first antibody, and about 1 µg of anti-CD16-PC7, the additional antibody labeled with the same fluorochrome. The reaction mixture was then contacted with approximately 1.25 µg/ml of the nucleic acid dye (Acridine Orange), which has an emission spectrum that overlaps with the emission spectra of PC7. This reaction mixture is mixed briefly and incubated at room temperature for approximately 10 minutes.

This reaction mixture is then reacted for about 8 seconds with the lytic system (about 600 µL of Immunoprep™ reagent A; see U.S. Pat. No. 5,030,554) that differentially lyses the non-nucleated red blood cells in the blood specimen while conserving the desired intrinsic and extrinsic properties of the leukocyte populations. After about 8 seconds, the quenching reagent (Immunoprep™ reagent B; 265 µL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module.

Figure 7A:
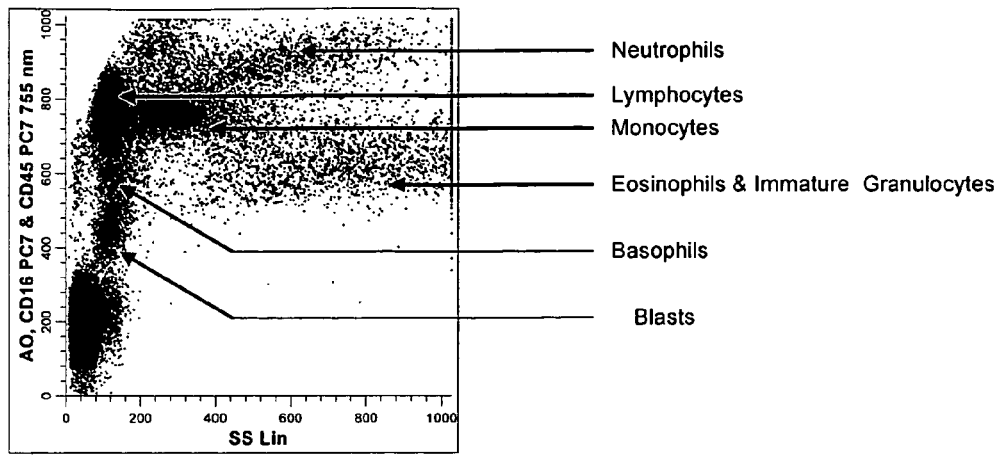
FIG. 7A is a two parameter histogram generated from the experiment described in Example 7, displaying AO, CD16-PC7 & CD45-PC7 fluorescence at a wavelength of approximately 755 nm vs SS. At least six cellular populations are identified and enumerated in this display: lymphocytes, monocytes, neutrophils, basophils, blasts and a cluster containing eosinophils and immature granulocytes.
Figure 7B:
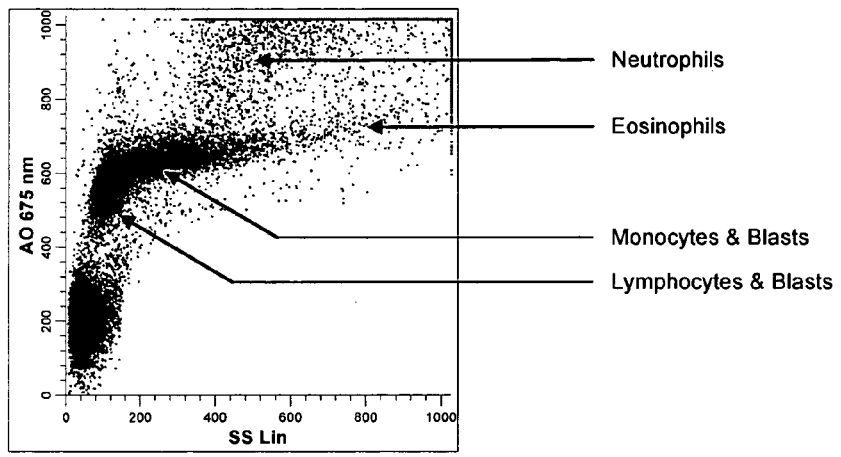
FIG. 7B is a two parameter histogram generated from the experiment described in Example 7, displaying AO fluorescence at a wavelength of approximately 675 nm vs SS. At least four cellular populations are identified and enumerated: eosinophils, neutrophils, a cluster containing lymphocytes and blasts and an additional cluster containing monocytes and blasts.
Figure 7C:
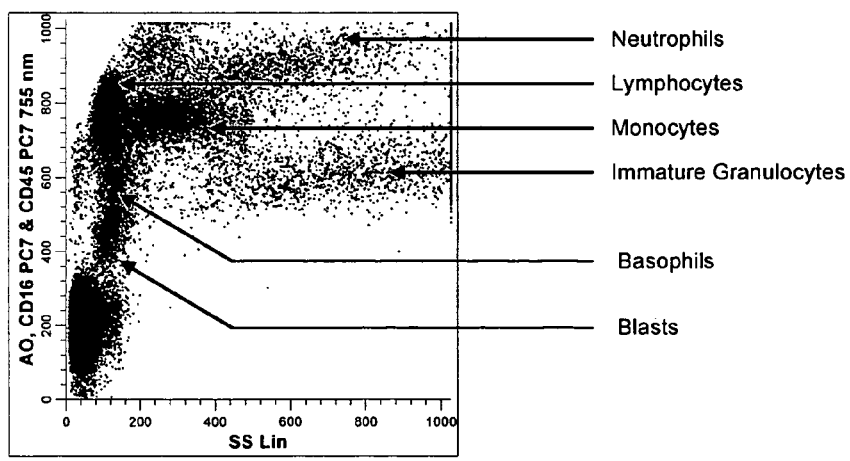
FIG. 7C is a two parameter histogram generated from the experiment described in Example 7, displaying AO, CD16-PC7 & CD45-PC7 fluorescence at a wavelength of approximately 755 nm vs SS following removal of the eosinophils by gating them out from FIG. 7B. At least six cellular populations are identified and enumerated in this display: lymphocytes, monocytes, neutrophils, basophils, blasts and immature granulocytes.

FIGS. 7A thru 7C are dual parameter histograms displaying the results of this analysis. FIG. 7A displays AO, CD16-PC7 & CD45-PC7 fluorescence at a wavelength of approximately 755 nm vs SS. At least six cellular populations are identified and enumerated in this display: lymphocytes, monocytes, neutrophils, basophils, blasts and a cluster containing eosinophils and immature granulocytes. FIG. 7B displays AO fluorescence at a wavelength of approximately 675 nm vs SS. At least four cellular populations are identified and enumerated: eosinophils, neutrophils, a cluster containing lymphocytes and blasts and an additional cluster containing monocytes and blasts. FIG. 7C display AO, CD16-PC7 & CD45-PC7 fluorescence at a wavelength of approximately 755 nm vs SS following removal of the eosinophils by gating them out from FIG. 7B. At least six cellular populations are identified and enumerated in this display: lymphocytes, monocytes, neutrophils, basophils, blasts and immature granulocytes.

Example 8

A single reaction mixture was prepared by reacting 100 µL of an abnormal human peripheral blood with about 1 µg of anti-CD45-PC7, the first antibody, and about 1 µg of anti-CD16-PE, the additional antibody labeled with a fluorochrome having a different emission spectrum from that of PC7. The reaction mixture was then contacted with approximately 1.25 µg/ml of Acridine Orange, which has an emission spectrum that overlaps with the emission spectra of PC7 and PE. This reaction mixture is mixed briefly and incubated at room temperature for approximately 10 minutes.

This reaction mixture is then reacted for about 8 seconds with the lytic system (about 600 µL of Immunoprep™ reagent A; see U.S. Pat. No. 5,030,554) that differentially lyses the non-nucleated red blood cells in the blood specimen while conserving the desired intrinsic and extrinsic properties of the leukocyte populations. After about 8 seconds, the quenching reagent (Immunoprep™ reagent B; 265 µL) is introduced into the mixture for 10 seconds, to terminate the lytic reaction. No fixation was used.

Thereafter, the mixture is allowed to flow into through a single flow aperture in a flow hematology analyzer that is capable of making multiple correlated measurements (fluorescent and optical) on cells as they pass through a single aperture in the transducer module.

Figure 8A:
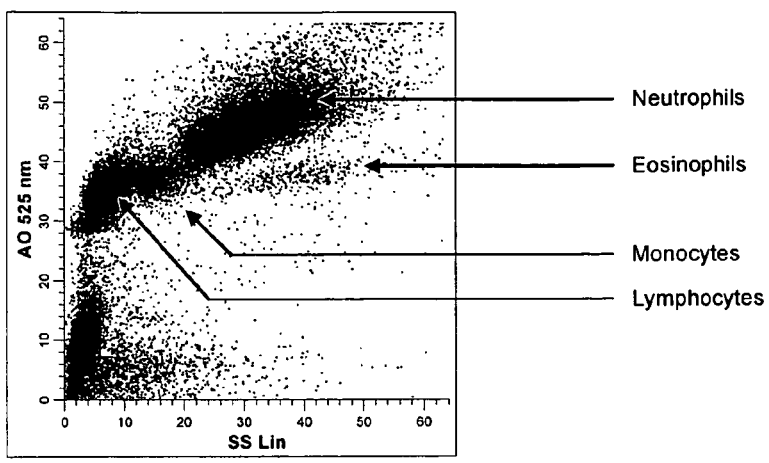
FIG. 8A is a two parameter histogram generated from the experiment described in Example 8, displaying AO fluorescence at a wavelength of approximately 525 nm vs SS. At least four cellular populations are identified and enumerated in this display: lymphocytes, monocytes, neutrophils and eosinophils.
Figure 8B:
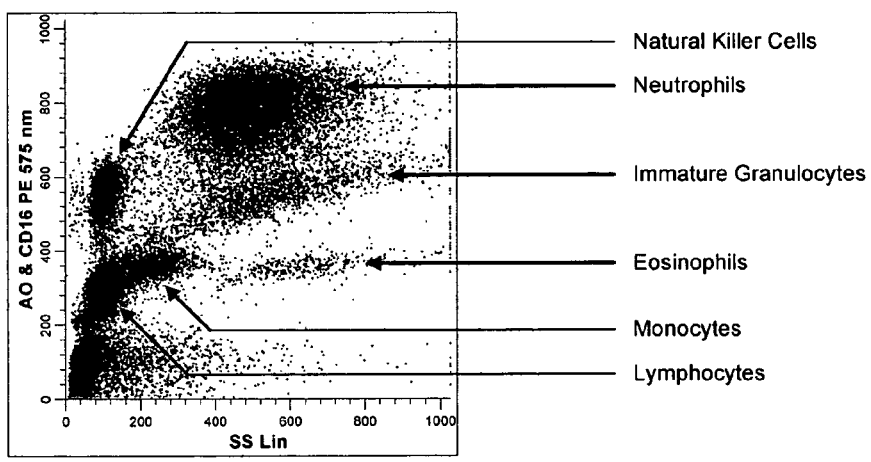
FIG. 8B is a two parameter histogram generated from the experiment described in Example 8, displaying AO & CD16-PE fluorescence at a wavelength of approximately 575 nm vs SS. At least six cellular populations are identified and enumerated: lymphocytes, monocytes, eosinophils, neutrophils, immature granulocytes and natural killer cells.
Figure 8C:
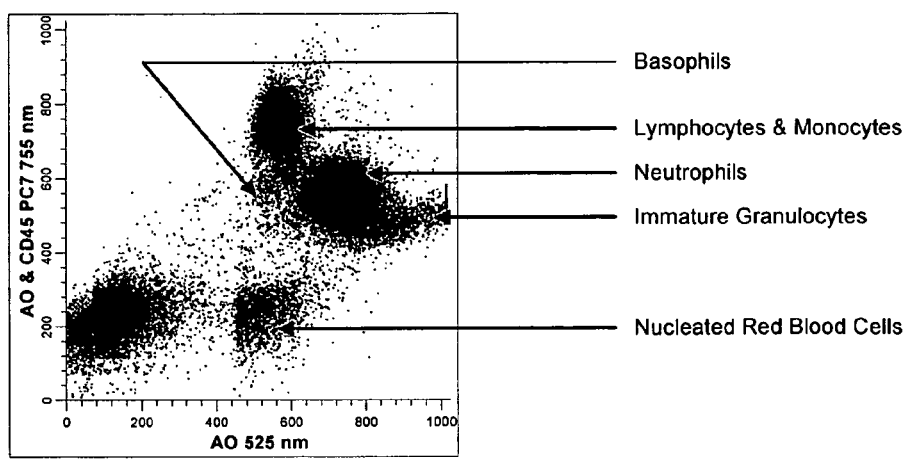
FIG. 8C is a two parameter histogram generated from the experiment described in Example 8, displaying AO & CD45PC7 fluorescence at a wavelength of approximately 755 nm vs AO fluorescence at a wavelength of approximately 525 nm. At least five cellular populations are identified and enumerated: a cluster containing lymphocytes and monocytes, basophils, neutrophils, immature granulocytes and nucleated RBCs.

FIGS. 8A thru 8C are dual parameter histograms displaying the results of this experiment. FIG. 8A displays AO fluorescence at a wavelength of approximately 525 nm vs SS. At least four cellular populations are identified and enumerated in this display: lymphocytes, monocytes, neutrophils and eosinophils. FIG. 8B displays AO & CD16-PE fluorescence at a wavelength of approximately 575 nm vs SS. At least six cellular populations are identified and enumerated: lymphocytes, monocytes, eosinophils, neutrophils, immature granulocytes and natural killer cells. FIG. 8C is a two parameter histogram generated from the experiment described in Example 8, displaying AO & CD45PC7 fluorescence at a wavelength of approximately 755 nm vs AO fluorescence at a wavelength of approximately 525 nm. At least five cellular populations are identified and enumerated: a cluster containing lymphocytes and monocytes, basophils, neutrophils, immature granulocytes and nucleated RBCs.

Example 9

A single reaction mixture was prepared by reacting 100 μL of an abnormal human peripheral blood specimen with about 1 μg of anti-CD45-PE, the first antibody, and about 1 μg of anti-CD16-PC7, the additional antibody labeled with a second fluorochrome having a different emission spectrum than PE. The reaction mixture was then contacted with approximately 1.25 μg/ml of Acridine Orange, which has an emission spectrum that overlaps with the emission spectra of PC7 and PE. This reaction mixture is mixed briefly and incubated at room temperature for approximately 10 minutes.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the leukocyte populations. After about 8 seconds, the quenching reagent (Immunoprep™ reagent B; 265 μL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module.

Figure 9A:
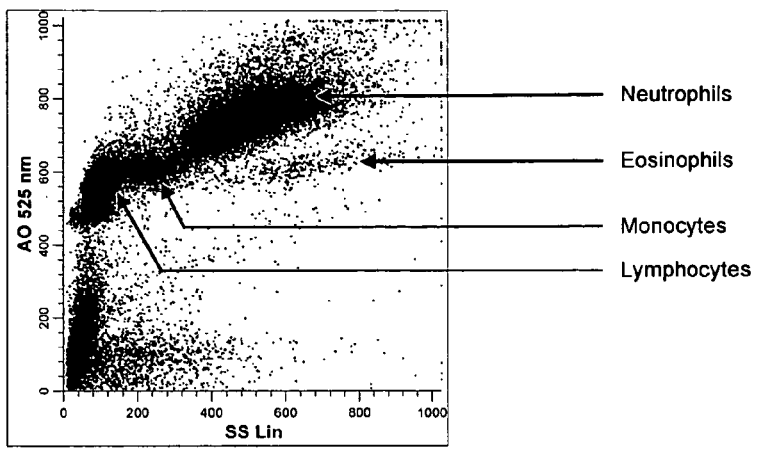
FIG. 9A is a two parameter histogram generated from the experiment described in Example 9, displaying AO fluorescence at a wavelength of approximately 525 nm vs SS. At least four cellular populations are identified and enumerated in this display: lymphocytes, monocytes, neutrophils and eosinophils.
Figure 9B:
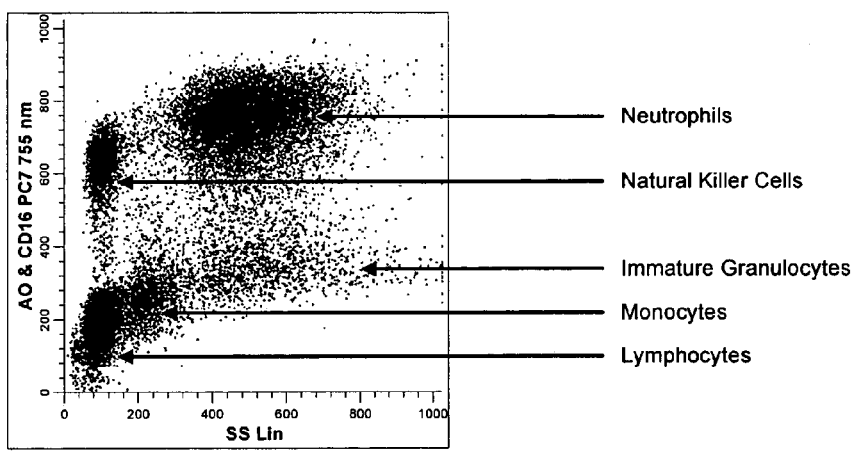
FIG. 9B is a two parameter histogram generated from the experiment described in Example 9, displaying AO & CD16-PC7 fluorescence at a wavelength of approximately 755 nm vs SS following removal of the eosinophils by gating them out from FIG. 9A. At least five cellular populations are identified and enumerated: lymphocytes, monocytes, neutrophils, immature granulocytes and natural killer cells.
Figure 9C:
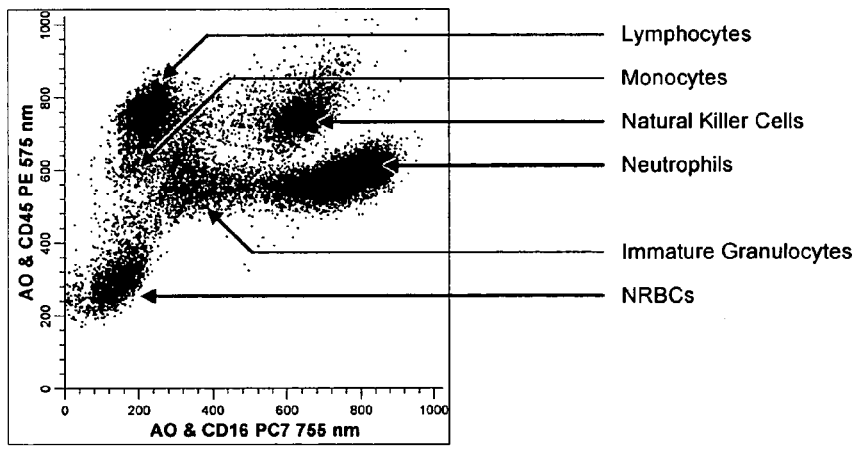
FIG. 9C is a two parameter histogram generated from the experiment described in Example 9, displaying AO & CD16-PC7 fluorescence at a wavelength of approximately 755 nm vs AO & CD45-PE fluorescence at a wavelength of approximately 575 nm following removal of the eosinophils by gating them out from FIG. 9A. At least six cellular populations are identified and enumerated: lymphocytes, monocytes, neutrophils, immature granulocytes, nucleated red blood cells and natural killer cells.

FIGS. 9A thru 9C are dual parameter histograms displaying the results of this analysis. FIG. 9A displays AO fluorescence at a wavelength of approximately 525 nm vs SS. At least four cellular populations are identified and enumerated in this display: lymphocytes, monocytes, neutrophils and eosinophils. FIG. 9B displays AO & CD16-PC7 fluorescence at a wavelength of approximately 755 nm vs SS following removal of the eosinophils by gating them out from FIG. 9A. At least five cellular populations are identified and enumerated: lymphocytes, monocytes, neutrophils, immature granulocytes and natural killer cells. FIG. 9C displays AO & CD16-PC7 fluorescence at a wavelength of approximately 755 nm vs AO & CD45-PE fluorescence at a wavelength of approximately 575 nm following removal of the eosinophils by gating them out from FIG. 9A. At least six cellular populations are identified and enumerated: lymphocytes, monocytes, neutrophils, immature granulocytes, nucleated red blood cells and natural killer cells.

In alternative assays in which anti-CD19 is employed as one of the antibodies of the method (data not shown), the effect of the presence of the anti-CD19 monoclonal is detected by the separation of the lymphocyte population into B and non-B cell populations. In atypical specimens this permits the observation of a distinction between B cell and non-B cell blasts, chronic and acute B cell disorders and the presence of atypical lymphocytes of B cell lineage.

This method may be used to detect blasts. Several optical and electrical parameters in conjunction with anti-CD45 fluorescence expression provide the necessary separation of blasts from normal cell types and debris, which is required to make this determination. Anti-CD19 antibody provides this method with the ability to categorize the blasts as lymphoid blasts of B cell lineage based on the expression of CD19. In exemplary abnormal blood specimens, the blasts can demonstrate CD19 expression that is higher than the non-B normal lymphocytes but equal to or less than that of the normal B cells in this specimen. Using this information, the blasts may be enumerated and categorized and then gated out of other views so that the normal 5-part differential may be recovered.

Other scattergrams may be generated on similar abnormal samples to detect blasts distinctly from debris and other cell types in the abnormal peripheral blood specimen. The blasts may be further characterized as being of non-B cell lineage. This is determined by scattergrams showing that the blasts display CD19 expression that is equal to or less than non-B cells.

Results from other analyses (not shown, but described in U.S. patent application No. 60/573,167, incorporated herein by reference) are also summarized in the examples below.

Example 10

The method of the present invention was conducted on four different biological specimens, i.e., (1) normal peripheral blood, (2) a B lymphoblastic leukemia specimen, (3) a B chronic lymphocytic leukemia (BCLL) specimen containing mostly small lymphocytes and (4) a BCLL with prolymphocytic transformation displaying a high percent of large lymphocytes. The method employed three antibodies, namely anti-CD45PECy5, anti-CD16PE and anti-CD19PE, according to the method including the lytic system described above in Examples 3 and 4. For each sample, five scattergrams were generated using the parameters as follows: DC vs. RLS, DC vs. Opacity (RF), fluorescence of anti-CD45PECy5 vs. SS, fluorescence of anti-CD45PECy5log vs. SS, and DC vs. fluorescence of CD16PE and CD19PE (data not shown).

The scattergrams of the normal sample illustrated the 5 normal populations of lymphocytes, basophils, eosinophils, neutrophils and monocytes, as well as B cell and non-B cell (lineage) populations.

The scattergrams of the B Cell lymphoblastic leukemia sample containing blasts of B cell lineage enumerated the normal 5 populations, as well as blasts, blasts of B-cell lineage, NK cells, and other B cells, and non-B cell populations.

The scattergrams of the B Cell chronic lymphocytic leukemia sample containing 1% atypical lymphocytes enumerated the normal 5 populations, as well as a population of numerous small B lymphocytes that do not exhibit a CD34 blast pattern and non-B cell populations. The method of this invention is able to correctly recategorize what the manual differential regarded as atypical lymphocytes as abnormal B cells. These leukemic cells may have a slightly lower CD45 expression than normal lymphocytes and most often are composed of small cells that also display impedance characteristics equal to or lower than small lymphocytes. When normal lymphocytes are present in significant numbers, or these types of CLL cells are present in relatively low numbers, this may result in a double lymphocyte peak in DC as well as in forward scatter. These cells, while slightly lower in CD45 expression, do not express the typical blast pattern (extremely weak or negative CD45 and increased scatter). Since these CLLs are almost always of B cell lineage (greater than 98 or 99%), they appear as CD19 positive cells.

The scattergrams of the B Cell chronic lymphocytic leukemia sample containing 52% atypical lymphocytes, by manual differential, demonstrate the same effect of recategorizing cells previously designated as atypical lymphocytes or blasts as abnormal large B cells. This less common variety of CLLs has a mixture of small and large lymphocytes. As in the variety that is predominantly small cells, these cells do not express the typical blast patterns that have been demonstrated and are almost always CD19 positive. Therefore these cells may be distinguished from blasts and other cell types found in peripheral blood by the method of the current invention.

Therefore the current invention has the ability to detect and identify blasts and this most prevalent variety of BCLL cells from each other as well as the other cell types found in peripheral blood. Non-BCLLs of this variety (small cells) will also be detected but appear as CD19 negative. These types of small cell CLLs may therefore also be described (flagged) electronically as atypical lymphocytes. This method therefore permits positive detection of the most clinically significant varieties of atypical lymphocytes as well as distinguishing between different forms of atypical lymphocytes (blast vs CLL cells) vs. activated cells. Thus this method clarifies the diagnosis of these disorders.

Previous experiments compared the results of pathology consultations based upon combining morphological examination with special stains, chromosomal analysis and leukemia phenotyping by traditional flow cytometry with use of the method of the present invention. Such comparison demonstrated that the method of this invention has an excellent ability to distinguish between blasts of B cell and non-B cell lineages.

Although not shown, a scattergram of a normal peripheral blood sample, treated with AO and anti-CD45 PECy7 only, showed staining patterns in the 525 nm to 675 nm range the same as those observed for the specimen stained with AO alone. The staining pattern at 755 nm is the same as that observed for the specimen combined with CD45 PECy7 alone. These data are characteristic of the principal of additive fluorescence and the desired staining result that was achieved when simultaneously staining cells with AO and a conjugated antibody with an overlapping peak emission spectrum.

Example 11

An Extended Differential on a flow cytometry based hematology system is obtained by forming a reaction mixture as follows. 100 µl of peripheral blood sample that contains 18 percent immature granulocytes (9% myelocytes and 9% metamyelocytes) is combined with AO, anti-CD45 PECy7 and anti-CD16 PECy7 in the same concentrations as described in the Examples 1-9 above.

This reaction mixture is mixed briefly and incubated at room temperature for approximately 10 minutes. At the end of the incubation period the reaction mixture is exposed to a lytic reagent (lyse and quench) to eliminate non nucleated RBC from the analysis and then analyzed on a flow cytometry system capable of measuring 5 channels of fluorescence in combination with side scatter (90 degrees) and forward angle scatter (2-18 degrees). The example utilizes a blue argon ion laser as an excitation source for the fluorescence detection.

The data (not shown) is displayed with side scatter on the horizontal axis and fluorescence on the vertical axis. In the 755 nm fluorescence channel immature granulocytes can be identified as a population of cells with less fluorescence and greater side scatter than mature granulocytes. In contrast the mature and immature granulocyte populations have overlapping fluorescence signatures in the 525 nm and 675 nm channels. There is improved separation of monocytes in the 675 nm channel compared to the spatial separation observed in the 525 nm channel.

This improved separation of monocytes in the 675 nm channel was used to remove this population from the histogram presented for the 755 nm channel. This technique removed the monocyte population overlap and aided in the identification and enumeration of mature and immature granulocyte populations in the 755 nm channel.

Thus, the method of this invention is capable of identifying monocytes, mature granulocytes and immature granulocytes, as well as the other cell populations identified in the preceding examples.

Example 12

An Extended Differential on a flow cytometry based hematology system is obtained by forming a reaction mixture as follows. 100 µl of peripheral blood sample that contains predominantly blasts and a small number of lymphocytes is combined with AO, anti-CD45 PECy7 and anti-CD16 PECy7 in the same concentrations as described in Examples 1-9.

This reaction mixture is mixed briefly and incubated at room temperature for approximately 10 minutes. At the end of the incubation period the reaction mixture is exposed to a lytic reagent (lyse and quench) to eliminate non nucleated RBC from the analysis and then analyzed on a flow cytometry system capable of measuring 5 channels of fluorescence in combination with side scatter (90 degrees) and forward angle scatter (2-18 degrees). The example utilizes a blue argon ion laser as an excitation source for the fluorescence detection.

Data from three selected fluorescence channels (not shown) was displayed with side scatter on the horizontal axis and fluorescence on the vertical axis. It is evident from examination of the data in the 755 nm channel that blasts appear as a cell population with less fluorescence than lymphocytes but with a side scatter signature that is larger than most small lymphocytes. This pattern is due to the decreased expression of the CD45 antigen on blasts. It is also evident from examining the data provided by the 525 nm and 675 nm channels that the blasts patterns are overlapping the lymphocyte population and do not appear as a distinct population. In this example the blast specimen demonstrates a bimodal distribution in these channels which is due to the age or fragility of the specimen.

Example 13

An abnormal peripheral blood specimen containing immature granulocytes and blasts was stained with AO and CD45 PC7 and CD16PC7 (two different antibodies with the same fluorochrome overlapping with AO in the 755 nm region) according to the method of this invention and using the same concentrations as those of Example 1-9 above. Both specimen examples were lysed using the Immunoprep™ reagent system and specimen preparation was the same as that described in the prior examples.

The results of this analysis (not shown) indicate that the method of this invention is capable of identifying and enumerating multiple cellular abnormalities in a single analytical evaluation.

Example 14

A normal peripheral blood specimen was stained with AO and CD45 PC7 and CD16PC7 (two different antibodies with the same fluorochrome overlapping with AO in the 755 nm region) according to the method of this invention and using the same concentrations as those of Examples 1-9 above. An aliquot of the same specimen was stained with AO and CD45 PC7 & CD16 PE (two different antibodies with different fluorochromes overlapping different areas of the AO emission spectrum at 575 nm and 755 nm.) Both specimen examples were lysed using the Immunoprep™ reagent system and specimen preparation was the same as that previously described.

The results (not shown) indicate a difference in eosinophil/neutrophil separation depending upon the fluorochrome to which the CD16 antibody is conjugated. This demonstrates two distinct examples of the principal of additive fluorescence and offers different analytical opportunities for detection and enumeration of normal and atypical cell populations.

The above examples illustrate the principle of additive fluorescence in the channels that have peak emission overlap. By applying this technique it is possible to conserve those patterns in a specific fluorescence channel that are useful in obtaining specific information and alter or enhance the patterns in other fluorescence channels to obtain new information.

In summary, the disclosed invention provides novel analytical methods for determining comprehensive extended differentials. These methods combine the analytical advantages provided by nucleic acid dyes and monoclonal antibodies into a single unified approach that is superior to either method alone.

All published documents and references to patent application are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

The invention claimed is:

1. A method for the differentiation or enumeration of cell populations in a biological sample, said method comprising:
   A. passing through a flow aperture in a transducer that is capable of making multiple correlated measurements on cells, a mixture comprising:
      i. said biological sample;
      ii. a first antibody that binds to an antigenic determinant that is differentially expressed on leukocytes and non-leukocyte cells, said antibody labeled with a first fluorochrome having a first peak emission spectrum,
      iii. at least one additional antibody, which is
         (a) an additional antibody labeled with a fluorochrome having said first peak emission spectrum, wherein said additional antibody binds to an antigenic determinant that is differentially expressed on mature and immature granulocytes or myeloid cells;
         (b) an additional antibody labeled with an additional fluorochrome, wherein said additional antibody binds to an antigenic determinant that is differentially expressed on mature and immature granulocytes or myeloid cells, and wherein said additional fluorochrome has a peak emission spectrum distinguishable from said first peak emission spectrum; or
         (c) an additional antibody labeled with an additional fluochrome, wherein said additional antibody binds to an antigenic determinant that is differentially expressed on mature and immature granulocytes or myeloid cells, and wherein said additional fluorochrome has a peak emission spectrum that overlaps the first peak emission spectrum; and
      iv. a nucleic acid dye which has a peak emission spectrum that overlaps the peak emission spectrum of at least one of said first fluorochrome and said additional fluorochrome;
   B. detecting the fluorescence signals of said fluorochromes and nucleic acid dye and detecting at least one additional parameter which is an optical parameter, an electrical parameter, or combinations thereof, for the cells in the sample; and
   C. analyzing the fluorescence of said nucleic acid dye and said fluorochromes at an emission wavelength within the overlapping peak emission spectra that reveals additive fluorescence, with said at least one additional parameter to differentiate or enumerate populations of hematological cells in said biological sample.

2. The method according to claim 1, wherein said first and additional fluorochromes are the same or different, and wherein the fluorochromes are independently dyes excitable by red radiation, or dyes excitable by blue radiation, or dyes excitable by green radiation, or combinations thereof.

3. The method according to claim 1, wherein said at least one channel of fluorescence is excited with a blue laser, a green laser, or a red laser.

4. The method according to claim 1, wherein said nucleic acid dye is a cell-permeant dye.

5. The method according to claim 1, further comprising contacting said mixture with a sphering agent.

6. The method according to claim 1, wherein said first antibody's antigenic determinant is expressed only on mature leukocytes, only on immature leukocytes, or is expressed differently on a population of mature leukocytes than it is expressed on a population of immature leukocytes.

7. The method according to claim 1, wherein said reporting comprises correlating transducer measurements of at least two parameters which are fluorescence, an optical parameter, an electrical parameter, or combinations thereof for each cell population.

8. The method according to claim 1, comprising contacting said mixture with a lytic reagent that differentially lyses non-nucleated red blood cells in said sample and conserves the leukocyte populations in said sample.

9. The method according to claim 8 further comprising retarding the effect of said lytic reagent by introducing a quenching or fixation reagent into said biological sample prior to said passing step.

10. The method according to claim 1, wherein said first antibody and said additional antibody are labeled with the same fluorochrome.

11. The method according to claim 1, wherein said first antibody and said additional antibody have differently detectable or non-overlapping peak emission spectra.

12. The method according to claim 1, wherein said first antibody and said additional antibody are labeled with fluorochromes having overlapping emission spectra.

13. The method according to claim 12, wherein said first antibody and said additional antibody are labeled with fluorochromes having overlapping peak emission spectra.

14. The method according to claim 1, wherein said nucleic acid dye is a cell-impermeant dye and said mixture further comprises a reagent that permeabilizes cells.

* * * * *

UNITED STATES PATENT AND TRADEMARK OFFICE
CERTIFICATE OF CORRECTION

PATENT NO. : 7,625,712 B2
APPLICATION NO. : 11/130492
DATED : December 1, 2009
INVENTOR(S) : Paul et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 653 days.

Signed and Sealed this

Second Day of November, 2010

David J. Kappos
*Director of the United States Patent and Trademark Office*